US011523766B2

(12) United States Patent
MacIver et al.

(10) Patent No.: US 11,523,766 B2
(45) Date of Patent: Dec. 13, 2022

(54) SYSTEMS AND METHODS OF ANALYZING AND DISPLAYING AMBULATORY ECG DATA

(71) Applicant: Spacelabs Healthcare L.L.C., Snoqualmie, WA (US)

(72) Inventors: Alasdair MacIver, Linlithgow (GB); Matthew Watson, Edinburgh (GB); Ruth Durie, Edinburgh (GB); Ryan McBroom, Carluke (GB); Grant McGeoghie, Edinburgh (GB); Stephen Wisniewski, Edinburgh (GB); Anuradha Chayanam, South Gyle (GB); Graham Prescott, Cambridge (GB)

(73) Assignee: Spacelabs Healthcare L.L.C., Snoqualmie, WA (US)

( * ) Notice: Subject to any disclaimer, the term of this patent is extended or adjusted under 35 U.S.C. 154(b) by 119 days.

(21) Appl. No.: 16/911,889

(22) Filed: Jun. 25, 2020

(65) Prior Publication Data

US 2021/0401316 A1 Dec. 30, 2021

(51) Int. Cl.
*A61B 5/339* (2021.01)
*A61B 5/00* (2006.01)
(Continued)

(52) U.S. Cl.
CPC .............. *A61B 5/339* (2021.01); *A61B 5/316* (2021.01); *A61B 5/333* (2021.01); *A61B 5/352* (2021.01);
(Continued)

(58) Field of Classification Search
None
See application file for complete search history.

(56) References Cited

U.S. PATENT DOCUMENTS 3,608,545 A 9/1971 Novack
4,106,495 A 8/1978 Kennedy
(Continued)

FOREIGN PATENT DOCUMENTS

EP 0845240 A1 6/1998
EP 1221299 A1 7/2002
(Continued)

OTHER PUBLICATIONS

International Search Report for PCT/US20/39550, dated Sep. 4, 2020.
(Continued)

*Primary Examiner* — Kennedy Schaetzle
(74) *Attorney, Agent, or Firm* — Novel IP

(57) ABSTRACT

This specification describes methods of performing ECG analyses. In one approach, the system receives an ECG recording for a first duration, automatically performs a first analysis of the ECG recording for the first duration to detect events with reference to each of a plurality of arrhythmias, generates a GUI where areas within the GUI are designated for displaying detected events for each of the arrhythmias and enables a user to select at least one ECG segment of a second duration of the ECG recording. In response to the user's selection of the at least one ECG segment, the system presents the user with at least one option, and in response to the user's selection of the option, the system performs a second analysis of the ECG segment of the second duration and displays at least one output corresponding to the second analysis.

23 Claims, 25 Drawing Sheets

(51) Int. Cl.
  *A61B 5/316* (2021.01)
  *A61B 5/333* (2021.01)
  *A61B 5/352* (2021.01)
  *A61B 5/361* (2021.01)
  *A61B 5/363* (2021.01)
  *A61B 5/364* (2021.01)
  *A61B 5/366* (2021.01)

(52) U.S. Cl.
  CPC .............. *A61B 5/361* (2021.01); *A61B 5/363* (2021.01); *A61B 5/364* (2021.01); *A61B 5/366* (2021.01); *A61B 5/4818* (2013.01)

(56) References Cited

U.S. PATENT DOCUMENTS

| | | |
|---|---|---|
| 4,121,575 A | 10/1978 | Mills |
| 4,318,412 A | 3/1982 | Stanly |
| 4,569,357 A | 2/1986 | Sanz |
| 4,850,370 A | 7/1989 | Dower |
| 5,058,598 A | 10/1991 | Nicklas |
| 5,322,069 A | 6/1994 | Gallant |
| 5,490,515 A | 2/1996 | Mortara |
| 5,511,553 A | 4/1996 | Segalowitz |
| 5,678,545 A | 10/1997 | Stratbucker |
| 5,687,717 A | 11/1997 | Halpern |
| 5,711,304 A | 1/1998 | Dower |
| 5,938,597 A | 8/1999 | Stratbucker |
| 6,052,615 A | 4/2000 | Feild |
| 6,119,035 A | 9/2000 | Wang |
| 6,327,487 B1 | 12/2001 | Stratbucker |
| 6,453,186 B1 | 9/2002 | Lovejoy |
| 6,463,320 B1 * | 10/2002 | Xue ............... A61B 5/7475 600/523 |
| 6,480,733 B1 | 11/2002 | Turcott |
| 6,490,479 B2 | 12/2002 | Bock |
| 6,519,490 B1 | 2/2003 | Wiesel |
| 6,532,379 B2 | 3/2003 | Stratbucker |
| 6,597,943 B2 | 7/2003 | Taha |
| 6,690,967 B2 | 2/2004 | Meij |
| 6,871,089 B2 | 3/2005 | Korzinov |
| 6,922,584 B2 | 7/2005 | Wang |
| 7,006,865 B1 | 2/2006 | Cohen |
| 7,020,514 B1 | 3/2006 | Wiesel |
| 7,031,765 B2 | 4/2006 | Ritscher |
| 7,120,485 B2 | 10/2006 | Glass |
| 7,146,206 B2 | 12/2006 | Glass |
| 7,194,300 B2 | 3/2007 | Korzinov |
| 7,277,752 B2 | 10/2007 | Matos |
| 7,566,307 B2 | 7/2009 | Inukai |
| 7,756,722 B2 | 7/2010 | Levine |
| 8,027,846 B2 | 9/2011 | Schoenberg |
| 8,147,419 B2 | 4/2012 | Krauss |
| 8,344,847 B2 | 1/2013 | Moberg |
| 8,674,837 B2 | 3/2014 | Gilham |
| 9,152,765 B2 | 10/2015 | Gilham |
| 9,629,566 B2 | 4/2017 | Gilham |
| 10,699,811 B2 | 6/2020 | Gilham |
| 11,139,077 B2 | 10/2021 | Gilham |
| 2002/0035334 A1 | 3/2002 | Meij |
| 2002/0045837 A1 | 4/2002 | Wei |
| 2002/0196141 A1 | 12/2002 | Boone |
| 2003/0120164 A1 | 6/2003 | Nielsen |
| 2003/0125632 A1 * | 7/2003 | Takizawa ............... A61B 5/352 600/509 |
| 2004/0073128 A1 | 4/2004 | Hatlestad |
| 2004/0116813 A1 | 6/2004 | Selzer |
| 2004/0172078 A1 | 9/2004 | Chinchoy |
| 2004/0220629 A1 | 11/2004 | Kamath |
| 2005/0059896 A1 | 3/2005 | Drakulic |
| 2006/0084883 A1 | 4/2006 | Linker |
| 2006/0224071 A1 | 10/2006 | Stewart |
| 2006/0264769 A1 | 11/2006 | Satin |
| 2007/0120763 A1 | 5/2007 | Depaepe |
| 2008/0077027 A1 | 3/2008 | Allgeyer |
| 2008/0221418 A1 | 9/2008 | Al-Ali |
| 2008/0228089 A1 | 9/2008 | Cho |
| 2009/0076345 A1 | 3/2009 | Manicka |
| 2009/0076397 A1 | 3/2009 | Libbus |
| 2009/0131805 A1 | 5/2009 | Obrien |
| 2009/0190713 A1 | 7/2009 | Wai |
| 2010/0121157 A1 | 5/2010 | Espina |
| 2010/0298655 A1 | 11/2010 | Mccombie |
| 2010/0298656 A1 | 11/2010 | McCombie |
| 2010/0298661 A1 | 11/2010 | McCombie |
| 2010/0324384 A1 | 12/2010 | Moon |
| 2011/0190643 A1 | 8/2011 | Zhang |
| 2011/0245688 A1 | 10/2011 | Arora |
| 2011/0270058 A1 | 11/2011 | Price |
| 2012/0004563 A1 * | 1/2012 | Kim ............... A61B 5/259 600/509 |
| 2012/0101396 A1 | 4/2012 | Solosko |
| 2012/0108991 A1 | 5/2012 | Song |
| 2012/0203491 A1 | 8/2012 | Sun |
| 2013/0030258 A1 | 1/2013 | Cheung |
| 2013/0116514 A1 | 5/2013 | Kroner |
| 2016/0120445 A1 | 5/2016 | Peluso |
| 2016/0135700 A1 * | 5/2016 | Gregg ............... G06F 40/166 600/523 |
| 2017/0119274 A1 * | 5/2017 | Chakravarthy ........ A61B 5/366 |
| 2018/0052957 A1 * | 2/2018 | Finkelmeier ........... A61B 5/363 |
| 2019/0282823 A1 | 9/2019 | Freeman |
| 2020/0000357 A1 * | 1/2020 | Shimai ............... A61B 5/333 |
| 2020/0294660 A1 | 9/2020 | Gilham |
| 2020/0303067 A1 | 9/2020 | Gilham |

FOREIGN PATENT DOCUMENTS

| | | |
|---|---|---|
| EP | 1221299 A2 | 7/2002 |
| WO | 9202171 A1 | 2/1992 |
| WO | 9955228 A1 | 11/1999 |
| WO | 0160250 A1 | 8/2001 |
| WO | 03099115 A1 | 12/2003 |
| WO | 03099115 A2 | 12/2003 |
| WO | 2011119512 A1 | 9/2011 |
| WO | 2012125135 A1 | 9/2012 |

OTHER PUBLICATIONS

Written Opinion of the International Searching Authority for PCT/US20/39550, dated Sep. 4, 2020.
Logan B, Healey J., 'Robust Detection of Atrial Fibrillation for a Long Term Telemonitoring System,' Computers in Cardiology 2005; 32:619-622.
Physician's Operation Manual, King of Hearts Express AF, Feb. 2004, http://www.instromedix.com/pdf/products/cardiac/KOHEX AF physician.pdf.
WIPO International Search Report dated Jan. 20, 2005, International Patent Application No. PCT/GB2004/003324, 6 pages.
"Ventricular Electrocardiography", Hurst, J.Willis, M.D. http://www.medscpae.com, 1998, pp. 1-131.
"Ventricular Electrocardiography", Hurst, J.Willis, M.D. http://www.medscpae.com, 1998, pp. 132-262.
"Ventricular Electrocardiography," Hurst, J.Willis, M.D. http://www.medscape.com, 1998 260 pages.
International Search Report for PCT/US2011/029278, dated Aug. 2, 2011.
International Search Report, PCT/US2011/028007, dated Jul. 11, 2011, International Search Authority.

* cited by examiner

Lifescreen PRO Report

| Patient: AllFamilies IncAF - (AllFamiliesIncAF) | | |
|---|---|---|
| NHS number: | Case: | Date of birth: 19/07/1961 Recording start: 22/11/2019 00:00:00 ; Duration: 07:21:48 |
| Hospital / Practice: | Order: | Analysed time: 07:21:48 ; 0% artefact |
| Referring doctor: | Ward | Analysed by: |
| Gender: Male | | |
| Primary indication: Test recording showing examples of all event types | | |

Analysis Results

The analysed recording lasted 7 hours 21 minutes 48 seconds, 0% of this period was excluded due to artefact.
Overall Ventricular beat burden was <1%. Overall Supraventricular beat burden was <1%.
The 10 second HR range was 34 - 126 bpm, the average 10 seconds HR was 67 bpm.
The time spent in Tachycardic rates at or above 100 bpm was 7 minutes 0 seconds, (1.58% of the analysed recording).
2 episodes of AF detected, total time spent in AF: 03:00:01. The AF burden was 40.75% of the analysed recording. Most severe event lasted 2 hours 0 minutes 1 second with a HR Range of 60 - 85 bpm.
6 episodes of Pause detected, longest event lasted 4.70 seconds.
4 episodes of Long R-R Interval detected.
9 episodes of VT detected, total time spent in VT: 19.50 seconds. Most severe event lasted 2.46 seconds with a HR Range of 117 - 122 bpm.
17 episodes of V-Run detected, total time spent in V-Run: 1 minute 17 seconds. Most severe event lasted 4.50 seconds with a HR Range of 78 - 80 bpm.
9 episodes of SVT detected, total time spent in SVT: 19.57 seconds. Most severe event latsed 2.53 seconds with a HR Range of 142 - 142 bpm.
3 episodes of SV-Run detected, total time spent in SV-Run: 4.50 seconds. Most severe event lasted 2.00 seconds with a HR Range of 120 - 120 bpm.
7 episodes of Bradycardia were detected, total time spent in Bradycardia: 1 minute 0 seconds. Longest event lasted 10.72 seconds with a HR Range of 33 - 34 bpm. Slowest event lasted 8.98 seconds with a HR Range of 33 - 33 bpm.
Bigeminy and Trigeminy patterns observed.

FIG. 5A

Lifescreen PRO Report

| Patient: AllFamilies IncAF - (AllFamiliesIncAF) | | Date of birth: 19/07/1961 | Gender: Male |
|---|---|---|---|
| NHS number: | Case: | Recording start: | 22/11/2019 00:00:00 ; Duration: 07:21:48 |
| Hospital / Practice: | Order: | Analysed time: | 07:21:48 ; 0% artefact |
| Referring doctor: | Ward | Analysed by: | |

Primary indication: Test recording showing examples of all event types

Analysis Comments
Please review the contents of the Ventricular section.
The analysed recording lasted 7 hours 21 minutes 48 seconds, 0% of this period was excluded due to artefact.
Overall Ventricular beat burden was <1%. Overall Supraventricular beat burden was <1%.
The 10 second HR range was 34 - 126 bpm, the average 10 seconds HR was 67 bpm.
The time spent in Tachycardic rates at or above 100 bpm was 7 minutes 0 seconds, (1.58% of the analysed recording).
2 episodes of AF detected, total time spent in AF: 03:00:01. The AF burden was 40.75% of the analysed recording. Most severe event lasted 2 hours 0 minutes 1 second with a HR Range of 60 - 85 bpm.
6 episodes of Pause detected, longest event lasted 4.70 seconds.
4 episodes of Long R-R Interval detected.
9 episodes of VT detected, total time spent in VT: 19.50 seconds. Most severe event lasted 2.46 seconds with a HR Range of 117 - 122 bpm.
17 episodes of V-Run detected, total time spent in V-Run: 1 minute 17 seconds. Most severe event lasted 4.50 seconds with a HR Range of 78 - 80 bpm.
9 episodes of SVT detected, total time spent in SVT: 19.57 seconds. Most severe event latsed 2.53 seconds with a HR Range of 142 - 142 bpm.
3 episodes of SV-Run detected, total time spent in SV-Run: 4.50 seconds. Most severe event lasted 2.00 seconds with a HR Range of 120 - 120 bpm.
7 episodes of Bradycardia were detected, total time spent in Bradycardia: 1 minute 0 seconds. Longest event lasted 10.72 seconds with a HR Range of 33 - 34 bpm. Slowest event lasted 8.98 seconds with a HR Range of 33 - 33 bpm.
Bigeminy and Trigeminy patterns observed.

| Correlate | Event | Time | Symptom | Activity |
|---|---|---|---|---|
| ☑ | VT | Wed 12/02/2014 14:19:34 | | |
| ☐ | SV-Run | Wed 12/02/2014 14:19:43 | | |
| ☐ | Patient Button | Wed 12/02/2014 14:20:12 | | |
| ☐ | Long R-R Interval | Wed 12/02/2014 14:20:34 | | |
| ☐ | VT | Wed 12/02/2014 14:21:34 | | |
| ☐ | VT | Wed 12/02/2014 14:22:03 | | |
| ☑ | V-Run | Wed 12/02/2014 14:22:44 | | |
| ☐ | VT | Wed 12/02/2014 14:22:47 | | |
| ☐ | VT | Wed 12/02/2014 14:22:54 | | |

SYSTEMS AND METHODS OF ANALYZING AND DISPLAYING AMBULATORY ECG DATA

FIELD

The present application relates to ECG monitoring. More particularly, the present application relates to computer-implemented methods of analyzing ECG recordings of patients generated in an ambulatory monitoring environment and displaying results of the analyses through a plurality of interactive graphical user interfaces (GUIs).

BACKGROUND

ECGs (Electrocardiograms) are waveform depictions of electrical activity in the heart. The ECGs are depicted by time (ms) versus voltage (μV) waveforms and are useful in diagnosing an extent to which cardiac problems exist in a patient. For example, ECGs are used in diagnosing cardiac arrhythmias (irregular heart rhythms), hyper and hypokalemia (high or low potassium levels, respectively), ischemia (loss of oxygen due to lack of blood flow possibly from blockage), myocardial infarction (heart attacks) and blockage.

Often, for a long duration ECG test, a healthcare practitioner provides a patient with an ambulatory ECG recording device, such as a Holter monitor, that is used to store ECG recordings of the patient. The patient wears ECG sensors for extended periods of time and the Holter monitor continuously records acquired signals. Such extended periods of time may range from 24 hours to several days. At the end of the extended period of time, the patient returns to the healthcare practitioner who removes the ECG sensors and retrieves the Holter monitor. Alternatively, the patient may remove the ECG sensors himself or herself and return the Holter monitor to the healthcare practitioner. A technician then typically uses an ECG software application to acquire data from the Holter monitor in order to study and analyze the ECG recordings of the patient.

While effective to continuously record patient ECG signals, conventional ECG recording systems have a number of disadvantages, however. First, they are difficult to reliably use for long periods of time. Accordingly, patients often do not use them consistently or correctly, resulting in long periods of unusable data. If the amount of unusable data exceeds a threshold, the acquired data is largely ineffective to making an accurate diagnosis of the patient. Unfortunately, whether the data is, or is not, sufficiently useable is often not discovered until a technician processes all of the data and manually determines if there is enough useable data to make a diagnosis. By that time, the patient has gone home and has to be called back to redo the ECG monitoring process.

Second, conventional devices record and present data chronologically. Therefore, a technician typically has to process the entirely of the recorded data before being able to accurately and comprehensively identify all meaningful events. This requires the technician to process a substantial amount of non-meaningful, or normal ECG data, and is therefore quite inefficient.

There is, therefore, a need for analytical techniques that enable a technician to process ECG recordings and gain meaningful insights into a patient's heart-related condition rapidly, if not immediately, upon receipt of the Holter monitor. It is also desirable to provide the technician with interactive interfaces that enable the technician to determine usability of ECG recordings, prioritize analyses and correlate analytical results with patient-recorded symptomatic events. It is further desirable to have a monitoring process that allows a technician to immediately know if there is a sufficient amount of useable data or if the patient has to redo the monitoring process. These, and other, objectives are addressed by the embodiments disclosed herein.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a computer readable non-transitory medium comprising a plurality of executable programmatic instructions wherein, when the plurality of executable programmatic instructions are executed by a processor, a process for prioritizing ECG analyses is performed, the plurality of executable programmatic instructions comprising: programmatic instructions, stored in the computer readable non-transitory medium, for receiving an ECG recording of a patient for a first duration; programmatic instructions, stored in the computer readable non-transitory medium, for automatically performing a first analysis of the ECG recording for the first duration to detect events indicative of at least one of a plurality of arrhythmias within the first duration; programmatic instructions, stored in said computer readable non-transitory medium, for generating a GUI, wherein the GUI is configured to display ECG waveforms corresponding to the first duration along with the automatically detected events indicative of at least one of the plurality of arrhythmias and wherein one of a plurality of areas within the GUI is designated for each of the plurality of arrhythmias; programmatic instructions, stored in the computer readable non-transitory medium, for enabling a user to select at least one of the ECG waveforms of a second duration; programmatic instructions, stored in the computer readable non-transitory medium, for presenting the user with at least one option in response to the user's selection of the at least one of the ECG waveforms; programmatic instructions, stored in said computer readable non-transitory medium, for performing a second analysis of the at least one of the ECG waveforms of the second duration in response to the user's selection of the at least one option; and programmatic instructions, stored in said computer readable non-transitory medium, for displaying at least one output corresponding to the second analysis.

The first duration may be up to 30 days.

Optionally, the plurality of arrhythmias comprises at least one of atrial fibrillation (AF), sinus pause or arrest, long R-R intervals, ventricular tachycardia (VT), ventricular run (V-Run), supraventricular tachycardia (SVT), supraventricular run (SV-Run), bradycardia or V-pattern including at least one of bigeminies and trigeminies.

Optionally, each of the automatically detected events is displayed as a vertical line and a width of each of the vertical lines is indicative of a duration of the automatically detected events.

The second duration may be up to 7 days.

Optionally, the second analysis comprises performing at least one of a ST-analysis, a QT-analysis, a heart rate variability analysis, a screening of recordings for sleep apnea, or a superimposition of heartbeats.

Optionally, the GUI is configured to display ECG waveform segments corresponding to each of the automatically detected events. Optionally, the GUI is configured to display the ECG waveform segments in a descending order of severity, as determined based on their corresponding automatically detected events. Optionally, the GUI is adapted to display up to 10 ECG waveform segments. Optionally, the GUI is adapted to be updated with an ECG waveform segment for a next most severe detected event if a displayed ECG waveform segment is deleted or if its severity is re-classified. Optionally, the computer readable non-transitory medium further comprises programmatic instructions for generating a visible area to display a composite ECG waveform comprising of a selected ECG waveform segment and ECG waveforms corresponding to a predetermined time duration before and/or after the selected ECG waveform segment.

Optionally, the GUI is adapted to display a count of a total number of automatically detected events.

Optionally, the computer readable non-transitory medium further comprises programmatic instructions for generating a plurality of data based on the first analysis and for automatically generating textual information using the plurality of data, wherein the plurality of data includes at least one of a total time duration of the ECG recording analyzed, a percentage of the total time duration excluded due to artifacts, a ventricular beat burden, a supraventricular beat burden, a count of events detected for each of a plurality of arrhythmias, or one or more statistics related to the events detected for each of the plurality of arrhythmias. Optionally, the computer readable non-transitory medium further comprises programmatic instructions for displaying, in the GUI, the generated textual information and programmatic instructions for integrating the textual information into a report upon selection of an option within the GUI. Optionally, the computer readable non-transitory medium further comprises programmatic instructions for dynamically updating the generated textual information if one or more automatically detected events are deleted or re-classified.

The present specification also discloses a method of prioritizing ECG analyses, the method comprising: receiving an ECG recording of a patient for a first duration; performing a first analysis of the ECG recording for the first duration to detect events with reference to each of a plurality of arrhythmias within the first duration; generating a GUI, said GUI displaying an ECG waveform corresponding to the first duration along with events detected with reference to each of the plurality of arrhythmias, wherein one of a plurality of areas within the GUI is designated for each of the plurality of arrhythmias; enabling a user to select at least one ECG segment of a second duration of the ECG recording; in response to the user's selection of the at least one ECG segment, presenting the user with at least one option; in response to the user's selection of the at least one option, performing a second analysis of the ECG segment of the second duration; and displaying output corresponding to the second analysis.

Optionally, the first analysis of the ECG recording is performed automatically.

Optionally, the events with reference to each of the plurality of arrhythmias is detected automatically.

The first duration may be up to 30 days.

Optionally, the plurality of arrhythmias comprises at least one of atrial fibrillation (AF), sinus pause or arrest, long R-R intervals, ventricular tachycardia (VT), ventricular run (V-Run), supraventricular tachycardia (SVT), supraventricular run (SV-Run), bradycardia, or V-pattern including at least one of bigeminies or trigeminies.

Optionally, each detected event is displayed as a vertical line and a width of each of the vertical lines is indicative of a time duration of the detected event.

The second duration may be up to 7 days.

Optionally, the second analysis comprises performing at least one of a ST-analysis, a QT-analysis, heartbeat analyses, a heart rate variability-analysis, a screening of recordings for sleep apnea, or a superimposition of heartbeats.

The present specification also discloses a method of displaying detected arrhythmia events, the method comprising: receiving an ECG recording of a patient; automatically performing an analysis of the ECG recording to detect events related to each of a plurality of arrhythmias; generating a GUI, wherein the GUI has a plurality of visible areas and wherein each of the plurality of visible areas is designated for displaying one of the plurality of arrhythmias; and displaying ECG waveform segments corresponding to detected events within each of the plurality of visible areas, wherein the ECG waveform segments within each of the plurality of areas are ordered in a descending order of severity of the related detected events.

Optionally, the plurality of arrhythmias comprises at least one of atrial fibrillation (AF), sinus pause or arrest, long R-R intervals, ventricular tachycardia (VT), ventricular run (V-Run), supraventricular tachycardia (SVT), supraventricular run (SV-Run), bradycardia or V-pattern including bigeminies and trigeminies.

Optionally, each of the plurality of visible areas displays up to 10 ECG waveform segments. Optionally, each of the plurality of visible areas is updated with an ECG waveform segment for a next most severe detected event if a displayed ECG waveform segment in the area is deleted or re-classified.

Optionally, the method further comprises displaying a count of a total number of detected events in each of the plurality of visible areas.

Optionally, if a displayed ECG waveform segment within at least one of the plurality of visible areas is selected, then generating a second GUI adapted to display a composite ECG waveform and wherein the composite ECG waveform comprises the selected ECG waveform segment and ECG waveforms corresponding to a predetermined time duration before and/or after the selected ECG waveform segment.

The present specification also discloses a system for displaying detected arrhythmia events, the system comprising: a plurality of electrodes configured to be positioned on a patient, wherein the plurality of electrodes is configured to acquire an ECG signal; an ambulatory device connected to the plurality of electrodes to receive and store the ECG signal as an ECG recording; a computing device comprising at least one processor and a computer readable non-transitory medium, wherein the computer readable non-transitory medium further comprises a plurality of executable programmatic instructions which, when executed, cause said at least one processor to: receive the ECG recording; automatically perform an analysis of the ECG recording to detect events related to each of a plurality of arrhythmias; generate a graphical user interface (GUI), wherein the GUI has a plurality of visible areas and wherein each of the plurality of visible areas is designated for one of the plurality of arrhythmias; and display ECG waveform segments corresponding to detected events within each of the plurality of visible areas, wherein the ECG waveform segments within each of the plurality of visible areas are ordered in a descending order of severity of the corresponding detected events.

Optionally, the plurality of arrhythmias comprises at least one of atrial fibrillation (AF), sinus pause or arrest, long R-R intervals, ventricular tachycardia (VT), ventricular run (V-Run), supraventricular tachycardia (SVT), supraventricular run (SV-Run), bradycardia or V-pattern including at least one of bigeminies and trigeminies.

Optionally, each of the plurality of visible areas is adapted to display up to 10 ECG waveform segments.

Optionally, each of the plurality of visible areas is adapted to be updated with an ECG waveform segment for a next most severe detected event if a displayed ECG waveform segment in the area is deleted or re-classified.

Optionally, a count of a total number of detected events is displayed in each of the plurality of visible areas.

Optionally, if a displayed ECG waveform segment within each of the plurality of visible areas is selected, then generating a second GUI to display a composite ECG waveform comprising of the selected ECG waveform segment and ECG waveforms corresponding to a predetermined time duration before and/or after the selected ECG waveform segment.

The present specification also discloses a method of generating and displaying textual information related to detected arrhythmia events, the method comprising: receiving an ECG recording of a patient; automatically performing an analysis of the ECG recording to generate a plurality of data; automatically generating textual information using the plurality of data; and generating a GUI to display the generated textual information, wherein the textual information is displayed in an area designated for the textual information within the GUI.

Optionally, the method further comprises, upon selection of an option within the GUI, integrating the textual information in an ECG analysis report. Optionally, the GUI comprises an input GUI configured to enable a user to edit the included textual information in the ECG analysis report.

Optionally, the method further comprises omitting the textual information from inclusion in an ECG analysis report.

Optionally, the method further comprises dynamically updating the displayed textual information if one or more detected events are deleted or re-classified.

Optionally, the plurality of data includes at least one of a total time duration of the ECG recording analyzed, a percentage of the total time duration excluded due to artifacts, a ventricular beat burden, a supraventricular beat burden, a count of events detected for each of a plurality of arrhythmias, or one or more statistics related to the events detected for each of the plurality of arrhythmias.

The present specification also discloses a system of generating and displaying textual information related to detected arrhythmia events, the system comprising: a plurality of electrodes positioned on a body surface of a patient, said plurality of electrodes configured to acquire an ECG recording; an ambulatory device connected to the plurality of electrodes to receive and store the ECG recording; a computing device including at least one processor and a computer readable non-transitory medium comprising a plurality of executable programmatic instructions which when executed cause said at least one processor to: receive the ECG recording of the patient; automatically perform an analysis of the ECG recording to generate a plurality of data; automatically generate textual information using the plurality of data; and generate a GUI to display the generated textual information, wherein the textual information is displayed in an area designated for the textual information within the GUI.

Optionally, upon selection of an option within the GUI, the system is configured to include the textual information in an ECG analysis report. Optionally, the plurality of executable programmatic instructions, when executed, further cause the at least one processor to generate a GUI to enable a user to edit the textual information in the ECG analysis report.

Optionally, the plurality of executable programmatic instructions, when executed, further cause the at least one processor to generate the ECG analysis report without the textual information.

Optionally, the plurality of executable programmatic instructions, when executed, further cause the at least one processor to automatically update the displayed textual information if one or more detected events are deleted or re-classified.

Optionally, the plurality of data includes at least one of a total time duration of the ECG recording analyzed, a percentage of the total time duration excluded due to artifacts, a ventricular beat burden, a supraventricular beat burden, a count of events detected for each of a plurality of arrhythmias, or one or more statistics related to the events detected for each of the plurality of arrhythmias.

The present specification also discloses a method of displaying patient-recorded events and detected arrhythmia events, the method comprising: receiving an ECG recording of a patient; receiving at least one patient-recorded event; automatically performing an analysis of the ECG recording to detect events with reference to each of a plurality of arrhythmias; determining if at least one detected event exists within a predetermined time window before and/or after the at least one patient-recorded event; generating a GUI to display, based on the determination, the at least one detected event together with the at least one patient-recorded event; enabling a user to manually correlate the at least one detected event with the at least one patient-recorded event; in response to the user manually correlating the at least one detected event with the at least one patient-recorded event, including an ECG waveform segment corresponding to the at least one detected event and an ECG waveform segment corresponding to the at least one patient-recorded event in an ECG analysis report; and in response to the user selecting the displayed at least one patient-recorded event, displaying, in the GUI, an ECG waveform segment corresponding to the selected at least one patient-recorded event along with an ECG waveform segment corresponding to the at least one detected event that the user manually correlated with the at least one patient-recorded event to form a composite ECG waveform.

Optionally, the predetermined time window ranges between 1 to 20 minutes before and/or between 1 to 10 minutes after the at least one patient-recorded event.

Optionally, the at least one detected event and the at least one patient-recorded event are displayed together in a chronological order.

Optionally, the predetermined time window is at least 3 minutes before and at least 3 minutes after the at least one patient-recorded event.

Optionally, the patent-recorded events correspond to symptomatic instances experienced by the patient. Optionally, the symptomatic instances are logged as a result of the patient actuating a button on an ECG recording device. The symptomatic instances may be logged by the patient in a paper diary.

The present specification also discloses a system of displaying patient-recorded events and detected arrhythmia events, the system comprising: a plurality of electrodes positioned on a body surface of a patient, said plurality of electrodes configured to acquire an ECG recording; an ambulatory device connected to the plurality of electrodes to receive and store the ECG recording; a computing device including at least one processor and a computer readable non-transitory medium comprising a plurality of executable programmatic instructions which when executed cause said at least one processor to: receive the ECG recording of the patient; receive at least one patient-recorded event; automatically perform an analysis of the ECG recording to detect events with reference to each of a plurality of arrhythmias; determine if at least one detected event exists within a predetermined time window before and/or after the at least one patient-recorded event; generate a GUI to display, based on the determination, the at least one detected event together with the at least one patient-recorded event; enabling a user to manually correlate the at least one detected event with the at least one patient-recorded event; in response to the user manually correlating the at least one detected event with the at least one patient-recorded event, include an ECG waveform segment corresponding to the at least one detected event and an ECG waveform segment corresponding to the at least one patient-recorded event in an ECG analysis report; in response to the user selecting the displayed at least one patient-recorded event, display, in the GUI, an ECG waveform segment corresponding to the selected at least one patient-recorded event along with an ECG waveform segment corresponding to the at least one detected event that the user manually correlated with the at least one patient-recorded event to form a compositive ECG waveform; and display, in the GUI, the composite ECG waveform.

Optionally, the predetermined time window ranges between 1 to 20 minutes before and/or between 1 to 10 minutes after the at least one patient-recorded event.

Optionally, the at least one detected event and the at least one patient-recorded event are displayed together in a chronological order.

Optionally, the predetermined time window is at least 3 minutes before and at least 3 minutes after the at least one patient-recorded event.

Optionally, the patent-recorded events correspond to symptomatic instances experienced by the patient. Optionally, the symptomatic instances are logged as a result of the patient actuating a button on the ambulatory device. Optionally, the symptomatic instances are logged by the patient in a paper diary.

The present specification also discloses a method of determining an endpoint of ECG analysis of an ECG waveform, wherein the endpoint of ECG analysis corresponds to a last region of usable detected ECG data, the method comprising: receiving an ECG recording of a patient; identifying an end point of the ECG recording; determining a start point of ECG activity in the ECG recording within a time duration preceding the end point; if no ECG activity is detected in the time duration, shifting the end point of the ECG recording to a start point of the time duration, wherein determining the start point of ECG activity and shifting of the end point of the ECG recording to the start point of the time duration are repeated until the start point of ECG activity is determined; if the start point of ECG activity is detected then establishing said start point as a start point of the last region of usable detected ECG data; and generating a GUI to display an ECG waveform corresponding to the ECG recording, wherein the last region of usable detected ECG data corresponds to the end point of ECG analysis on the ECG waveform.

The duration may range from 30 seconds to 120 seconds.

Optionally, a portion of the ECG recording comprising a flat line and/or noise is considered as having no ECG activity.

Optionally, the method further comprises providing an input configured to enable a user to manually shift the end point of ECG analysis to a desired position on the ECG waveform.

The present specification also discloses a system of setting an end point of ECG analysis, the system comprising: more than one electrode positioned on a patient, wherein the more than one electrode is configured to acquire an ECG signal; an ambulatory device connected to the more than one electrode, wherein the ambulatory device is configured to receive and store the ECG signal; a computing device having at least one processor and a computer readable non-transitory medium comprising a plurality of executable programmatic instructions which when executed cause said at least one processor to: receive the ECG recording of the patient; identify an end point of the ECG recording; determine a start point of ECG activity in the ECG recording within a time duration preceding the end point; if no ECG activity is detected in the time duration, shift the end point of the ECG recording to the start point of the time duration, wherein determining the start point of ECG activity and shifting of the end point of the ECG recording to the start point of the time duration are repeated for a plurality of periods of the time duration till the start point of ECG activity is detected; if the start point of ECG activity is detected then shift the end point of the ECG recording to the start point of the ECG activity; and generate a GUI to display an ECG waveform corresponding to the ECG recording, wherein the determined start point of ECG activity is determined to correspond to the end point of ECG analysis on the ECG waveform.

The duration may range from 30 seconds to 120 seconds.

Optionally, a ECG signal comprising a flat line and/or a noise is categorized as having no ECG activity.

Optionally, the plurality of executable programmatic instructions are further configured to cause said at least one processor to generate a GUI input adapted to enable a user to manually shift the end point of ECG analysis to a desired position on the ECG waveform.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1:
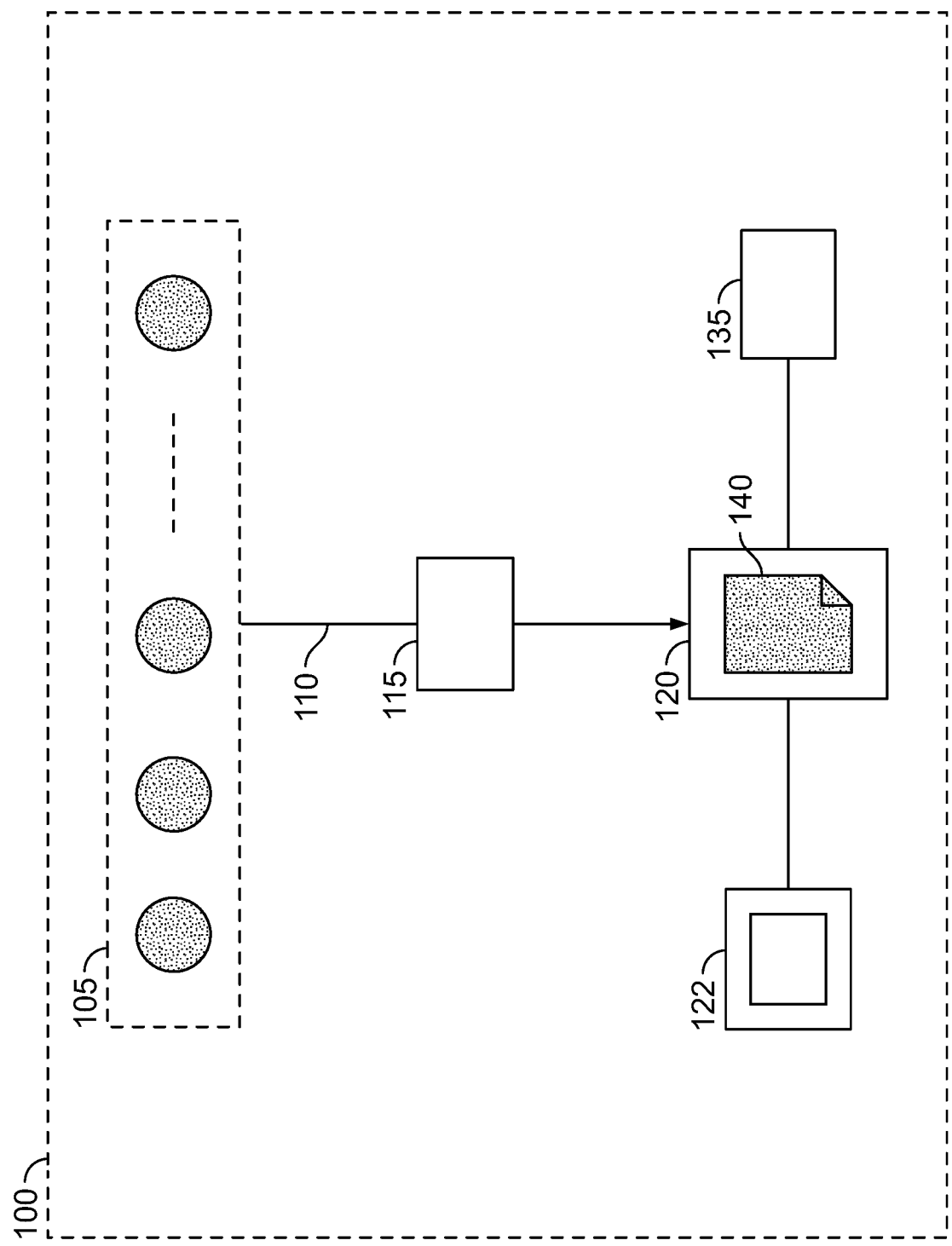
FIG. 1 is a block diagram illustration of an ECG monitoring, analysis and display a system, in accordance with some embodiments of the present specification.

The term "module or engine" used in this disclosure may refer to computer logic utilized to provide a desired functionality, service, or operation by programming or controlling a general purpose processor. In various embodiments, a module can be implemented in hardware, firmware, software or any combination thereof. The module may be interchangeably used with unit, logic, logical block, component, or circuit, for example. The module may be the minimum unit, or part thereof, which performs one or more particular functions.

In various embodiments, a "computing device" includes an input/output controller, at least one communications interface and system memory. In various embodiments, the computing device includes conventional computer components such as a processor, necessary non-transient memory or storage devices such as a RAM (Random Access Memory) and disk drives, monitor or display and one or more user input devices such as a keyboard and a mouse. In embodiments, the user input devices allow a user to select objects, icons, and text that appear on the display via a command such as a click of a button on a mouse or keyboard or alternatively by touch in embodiments where the display is a touch-enabled screen. The computing device may also include software that enables wireless or wired communications over a network such as the HTTP, TCP/IP, and RTP/RTSP protocols. These elements are in communication with a central processing unit (CPU) to enable operation of the computing device. In various embodiments, the computing device may be a conventional standalone computer, a mobile phone, a tablet or a laptop. In some embodiments, the functions of the computing device may be distributed across multiple computer systems and architectures.

In some embodiments, execution of a plurality of sequences of programmatic instructions or code enables or causes the CPU of the computing device to perform various functions and processes. In alternate embodiments, hard-wired circuitry may be used in place of, or in combination with, software instructions for implementation of the processes of systems and methods described in this application. Thus, the systems and methods described are not limited to any specific combination of hardware and software.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

FIG. 1 is a block diagram illustration of an ECG monitoring, analysis and display a system 100, in accordance with some embodiments of the present specification. The system comprises a group of electrodes 105 for attaching to a patient's body surface at specific sites. The group of electrodes 105 is configured to sense and acquire ECG (electrocardiogram) recording corresponding to electrical activity of the patient's heart.

In some embodiments, a plurality of cables 110 connects the group of electrodes 105 to a computing device 120 for receiving and storing the ECG recording. In some embodiments, an ambulatory ECG recording device 115 (such as, for example, a Holter monitor) may be used to record signals from the cables 110 for an extended period of time during an ECG test. At an end of the ECG test, the ECG recording device 115 may be connected (through a wireless or wired connection) to the computing device 120 to further store and process the ECG recording. The computing device 120 is also connected to at least one display 122 and a printer 135 to print ECG reports generated by the computing device 120.

In various embodiments, the computing device 120 implements an ECG processing module or engine 140 that executes a plurality of sequences of programmatic instructions or code to enable or cause at least one CPU of the computing device 120 to automatically analyze the ECG recording, display ECG waveforms and a plurality of analytical data corresponding to the ECG recordings and provide a plurality of functionalities to the user through one or more interactive GUIs (Graphical User Interfaces). The interactive GUIs are presented to the user on the at least one display 122. In embodiments, the ECG processing module 140 supports analysis of ECG recordings for duration of up to 30 days.

In some embodiments, the ECG processing module 140 is configured to automatically analyze ECG recordings, for a first duration, with reference to a first set of functionalities. In some embodiments, the first duration is up to 30 days. In some embodiments, the first set of functionalities comprise detection and display of events related to various categories of cardiac arrhythmias such as, but not limited to, atrial fibrillation (AF), sinus pause or arrest, Long R-R intervals, ventricular tachycardia (VT), ventricular run (V-Run), supraventricular tachycardia (SVT), supraventricular run (SV-Run), bradycardia and V-pattern including bigeminies and trigeminies.

In accordance with some aspects of the present specification, the ECG processing module 140 executes a plurality of sequences of programmatic instructions or code to enable the user to select ECG recordings for a second duration, mark or annotate the ECG recordings for the second duration and process the ECG recordings for the second duration with reference to a second set of functionalities. ECG recordings may be marked by receiving an input from a user through, for example, a mouse, touchpad, icon selection, or any other input mechanism and associating the user input with one or more data tags which are associated with one or more portions of the ECG recordings. In embodiments, the second duration is less than the first duration. In some embodiments, the second duration is up to 7 days. In some embodiments, the second set of functionalities comprise analyses such as those related to, but not limited to, ST-analysis, QT-analysis, Heart Rate Variability-analysis, heartbeat analyses, screening of recordings for Sleep Apnea, superimposition of heartbeats and enabling the user to reclassify cardiac beats/morphologies and/or detected events.

The analyses related to the second set of functionalities may be performed immediately or later. In some embodiments, the selected ECG recording for the second duration may be analyzed immediately—that is, as soon as the ECG recording for the second duration is selected—by invoking or opening an analysis session and applying the analytical programmatic instructions to the selected ECG recording segment. In alternate embodiments, the user is enabled to store the selected ECG recording for the second duration in a repository thereby allowing the analyses (related to the second set of functionalities) to be conducted at a later time (and perhaps on a different computing device and/or possibly by a different user).

It should be appreciated that the term "immediately" shall generally refer to an action taken after a prior triggering event without a substantive delay of time, such as an action taken in less than five minutes, 4 minutes, 3 minutes, 2 minutes, 1 minute, 30 seconds, or any increment therein, after the prior triggering event. It should be further appreciated that the term "automatically' shall generally refer to an action taken without further human or manual intervention by a user. Accordingly, a programmatic routine, executed by a software application, that is performed after a preceding programmatic routine without specifically being prompted by a user or manually activated by a user shall be considered "automatically" executed.

In some embodiments, the ECG recordings for the second duration are selected to encompass or include at least one ECG segment in the ECG recordings for the first duration. The second set of functionalities are then directed towards performing more detailed analyses or processing of the selected at least one ECG segment. In some embodiments, the ECG recordings for the second duration are selected to encompass or include at least one significant or pathological event detected in the ECG recordings for the first duration. In other words, the first set of functionalities are directed towards quickly identifying significant or pathological events while the second set of functionalities are directed towards performing more detailed analyses or processing of ECG recordings corresponding to the identified significant or pathological events. In some embodiments, however, the ECG recordings for the second duration are selected to encompass or include at least one noisy (of poor quality or low signal-to-noise ratio) ECG segment (and not necessarily a detected event) in the ECG recordings for the first duration. In such cases, the second set of functionalities are directed towards performing more detailed analyses or processing of the at least one noisy ECG segment.

This staged analysis, in first and second set of functionalities, enables 'triaging' of ECG recordings. Triaging involves assessment of ECG recordings to allow prioritizing of a full analysis involving both first and second set of functionalities, creation of analysis reports and diagnosis/treatment based on detected quality (signal-to-noise ratio) of ECG recordings and/or detected arrhythmias or other events and the significance of those events. Persons of ordinary skill in the art would understand that a substantial number of ECG recordings do not include instances of arrhythmia that a patient may actually be experiencing. In addition, persons of ordinary skill in the art would also understand that some ECG recordings do not possess ECG of sufficient quality or quantity to support an analysis.

The first set of functionalities enable the user to quickly identify if the ECG recordings are of sufficiently good quality and/or possess significant events or if the ECG recordings are typical of the many recordings that do not possess any significant arrhythmias or other events and/or are fraught with noisy or low quality ECG data. Thus, automatic detection of events in long duration ECG recordings (such as, for example, those of a duration up to 30 days), presentation or display of areas where target arrhythmias are present and extraction of ECG from those areas (for more detailed analyses through the second set of functionalities) may reduce wasted effort for clinicians and help accelerate diagnosis in cases where specific arrhythmias or conditions are suspect. Similarly, based on triaging if it is identified that the ECG recordings possess no events but instead include a substantial duration(s) of poor quality ECG data then, if the patient is close, the user may choose to have the patient participate in a second ECG acquisition test or stage.

Figure 2A:
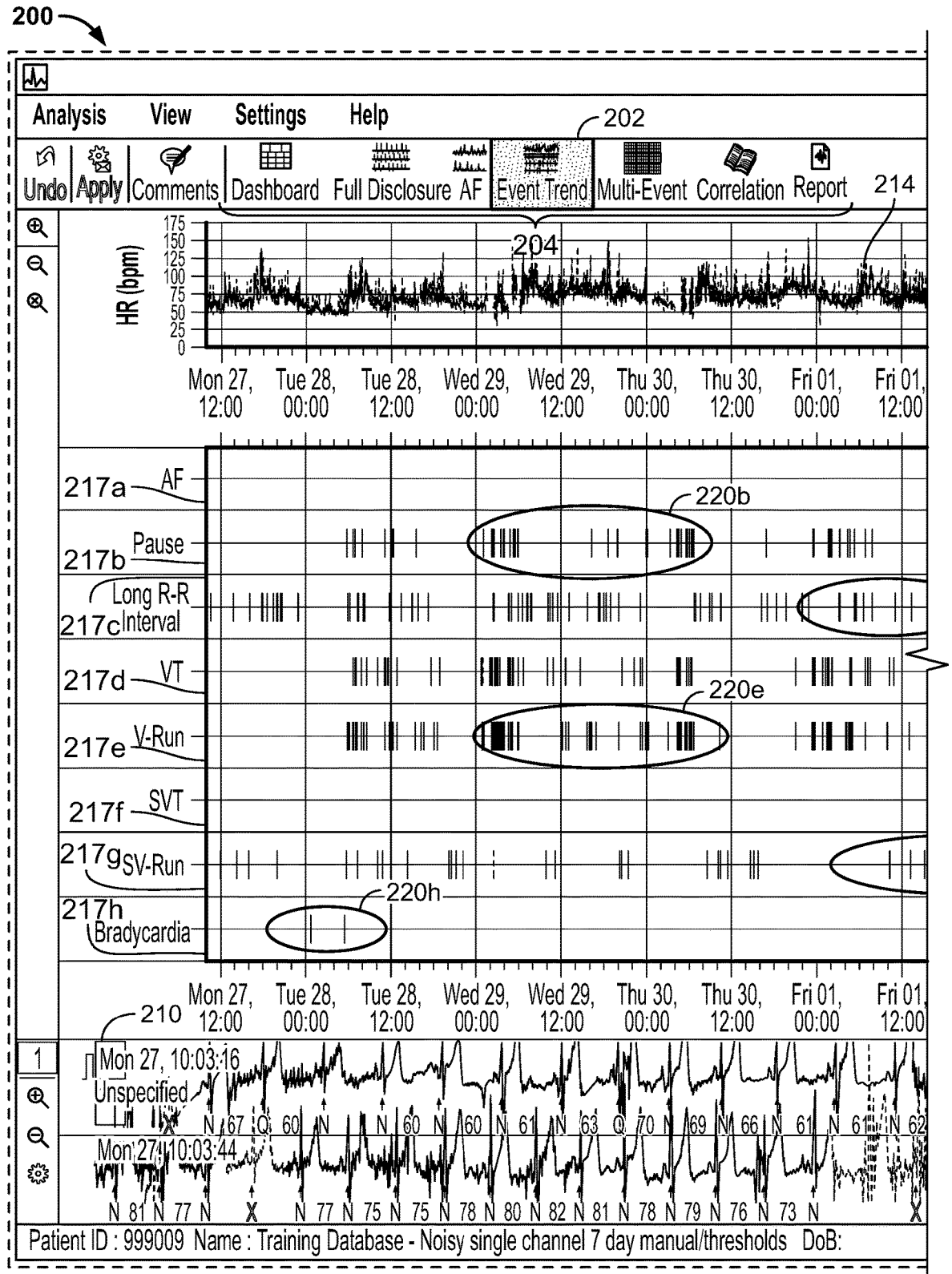
FIG. 2A shows a GUI screen configured to present one or more ECG event trends, in accordance with some embodiments of the present specification.
Figure 2A:
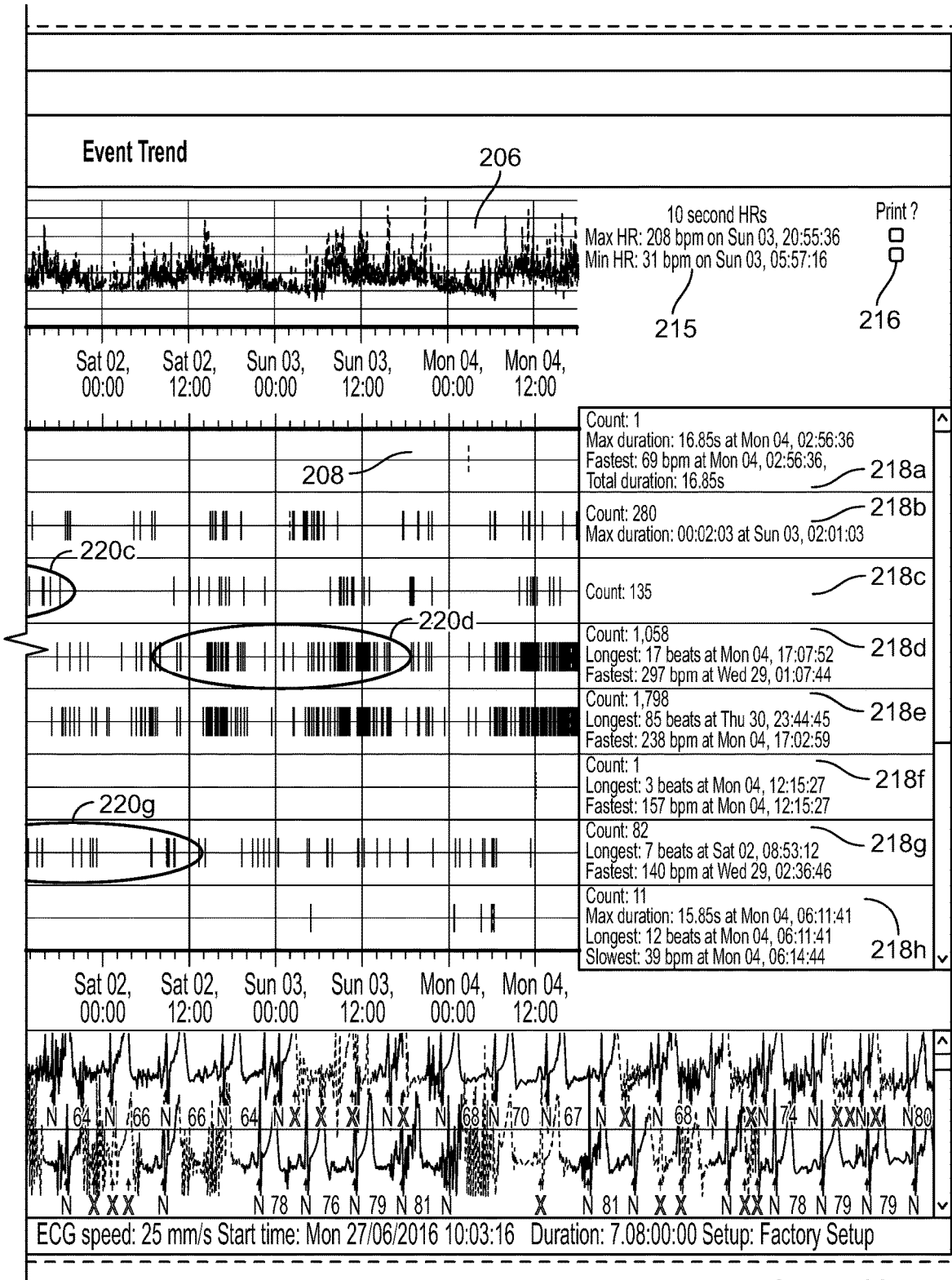

FIG. 2A shows a GUI screen 200 configured to present one or more ECG event trends, in accordance with some embodiments of the present specification. The ECG processing module 140 (FIG. 1) generates the GUI screen 200 in response to the user clicking an event trend icon or button 202 displayed on a main menu 204. In some embodiments, the GUI screen 200 is a composite interface having first, second and third sub-screens 206, 208 and 210. The first sub-screen 206 displays a heart rate (HR) range 214 corresponding to ECG data recordings for a first duration (predetermined or user-selected). In various embodiments, the first duration may be up to 30 days. In one embodiment, as an example, the HR range 214 being displayed corresponds to a period of 7 days. The HR range 214 is followed by a textual portion 215 that provides auto-generated notes such as, for example, maximum and minimum heart rates as well as the date and time of occurrence of the maximum and minimum heart rates. The user may select a checkbox 216 to enable printing of the textual portion 215 which may include printed strips of the maximum and/or minimum heart rates, for example.

The second sub-screen 208 displays detected events related to various categories of cardiac arrhythmias (and determined with reference to the first set of functionalities) occurring in the duration of the HR range 214. In some embodiments, a strip, area or row (within the sub-screen 208) is designated for presenting events detected and related to each category of the cardiac arrhythmias. In some embodiments, each of the events detected is displayed as a vertical line such that a width or thickness of the vertical line corresponds to the duration of the event it represents. The vertical lines, displayed within each strip, area or row, are indicative of when events of that category of cardiac arrhythmia have been detected within the duration of the HR range 214. The detected events presented as vertical lines resemble a 'pianola' display 208. It should be appreciated that a plurality of short events occurring close to each other may be perceived as a thick vertical line if the user has minimized the zoom level of the 'pianola' display 208. Thus, in such cases a width, a thickness, or any other dimension of the vertical line may correspond to the duration and/or frequency of the events it represents.

For example, strip 217a presents events detected related to atrial fibrillation (AF) and is followed by a textual portion 218a that provides auto-generated notes such as, for example, a count of the detected AF events, date and time stamped maximum duration amongst the detected AF events, total duration of the detected AF events and date and time stamped fastest beats per minute. Strip 217b presents events detected related to sinus pause or arrest and is followed by a textual portion 218b that provides auto-generated notes such as, for example, a count of the detected pause events and date and time stamped maximum duration amongst the detected pause events. The strip 217b displays a plurality of events in the form of vertical lines 220b representing occurrences of sinus pauses or arrests in the HR range 214.

Strip 217c presents events detected related to Long R-R Intervals (which may also be referred to as "dropped beats", in an embodiment) and is followed by a textual portion 218c that provides auto-generated notes such as, for example, a count of the detected Long R-R Intervals. The strip 217c displays events in the form of vertical lines 220c representing occurrences of Long R-R Intervals in the HR range 214. Strip 217d presents events detected related to ventricular tachycardia (VT) and is followed by a textual portion 218d that provides auto-generated notes such as, for example, a count of the detected VT events, date and time stamped longest event duration and date and time stamped fastest event. The strip 217d displays events in the form of vertical lines 220d representing occurrences of VT events in the HR range 214.

Strip 217e presents events detected related to ventricular run (V-run) and is followed by a textual portion 218e that provides auto-generated notes such as, for example, a count of the detected V-run events, date and time stamped longest event duration and date and time stamped fastest event. The strip 217e displays events in the form of vertical lines 220e representing occurrences of V-run events in the HR range 214. Strip 217f presents events detected related to supraventricular tachycardia (SVT) and is followed by a textual portion 218f that provides auto-generated notes such as, for example, a count of the detected SVT events. In this embodiment, there are no SVT events detected and therefore the portion 218f shows "no events". Also, the strip 217f does not display any vertical line representing occurrences of SVT events in the HR range 214.

Strip 217g presents events detected related to supraventricular run (SV-run) and is followed by a textual portion 218g that provides auto-generated notes such as, for example, a count of the detected SV-run events, date and time stamped longest event duration and date and time stamped fastest event. The strip 217g displays events in the form of vertical lines 220g representing occurrences of SV-run events in the HR range 214. Strip 217h presents events detected related to bradycardia and is followed by a textual portion 218h that provides auto-generated notes such as, for example, a count of the detected bradycardia events, date and time stamped maximum beat duration, date and time stamped longest beat duration and date and time stamped slowest heart rate. The strip 217h displays events in the form of vertical lines 220h representing occurrences of bradycardia events in the HR range 214.

In embodiments, the user can zoom in, or out of the 'pianola' display 208, allowing the user to see frequency/occurrence of events in finer resolution, and if the user selects or clicks on any vertical line (that is, a detected event) the ECG processing module 140 updates the third sub-screen 210 to display a corresponding ECG waveform to provide the user with more context of what happened in the ECG recording both before and after their selected or clicked event.

In some embodiments, the system 100 (FIG. 1) may include first and second displays (or screens) wherein the first display is configured to show the GUI screen 200 and the second display is configured to show a zoomed-in version of any of the HR range 214, ECG waveform 210 or vertical lines of the GUI screen 200. In such embodiments, if the user selects or clicks on any vertical line (that is, a detected event) or clicks within the HR range, ECG waveform in the sub-screens 206, 210, the ECG processing module 140 generates and presents, within another GUI in the second display, the selected or clicked point in the center of a composite ECG waveform comprising of an ECG waveform segment corresponding to the selected or clicked point along with a predetermined duration of ECG waveforms before and after the selected or clicked point. Presentation of the composite ECG waveform in the second display gives the user a wider window of ECG context prior to, and following the selected point.

Figure 2B:
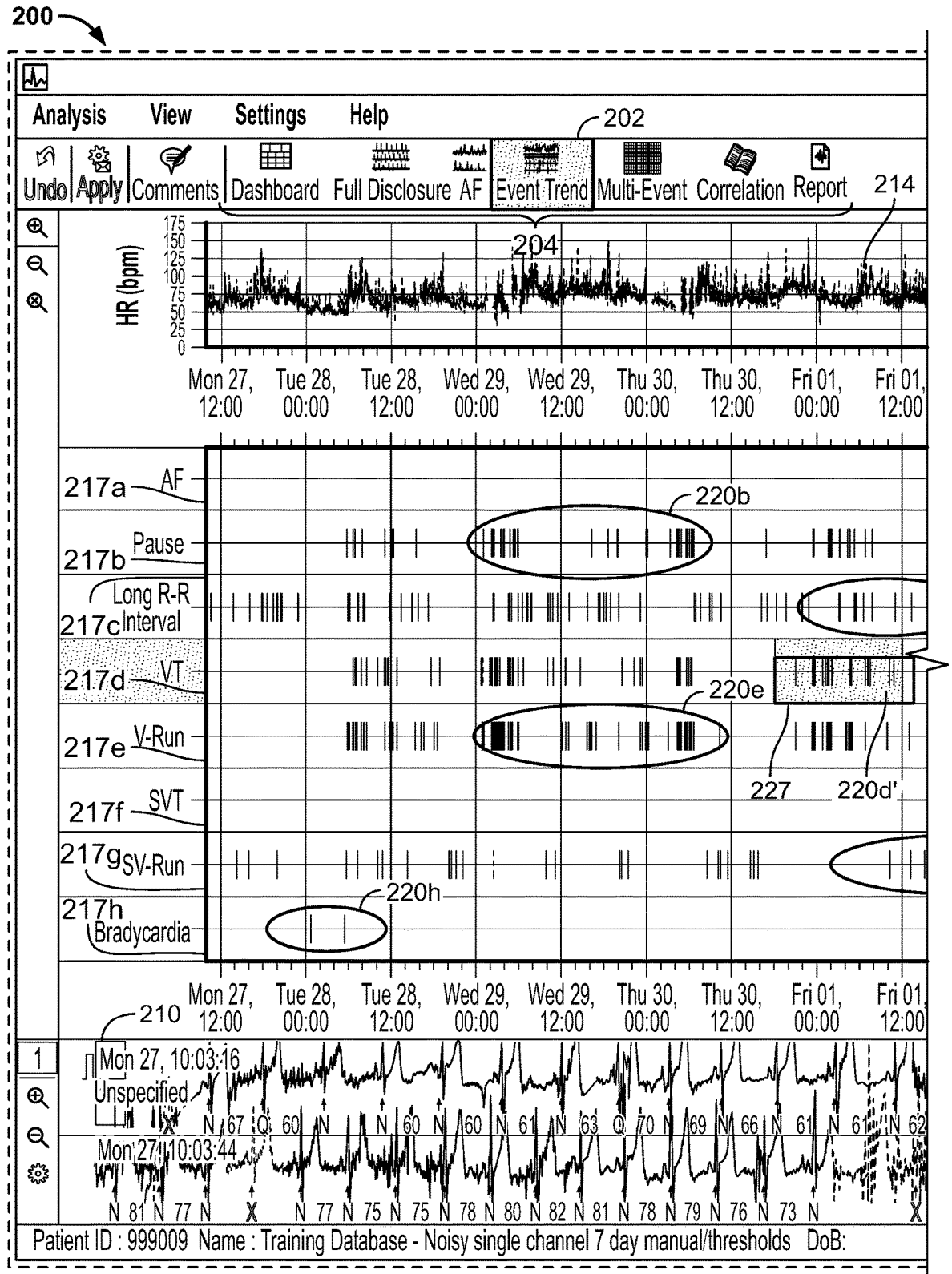
FIG. 2B shows the GUI screen of FIG. 2A with user-selected arrhythmia events for further analysis, in accordance with some embodiments of the present specification.
Figure 2B:
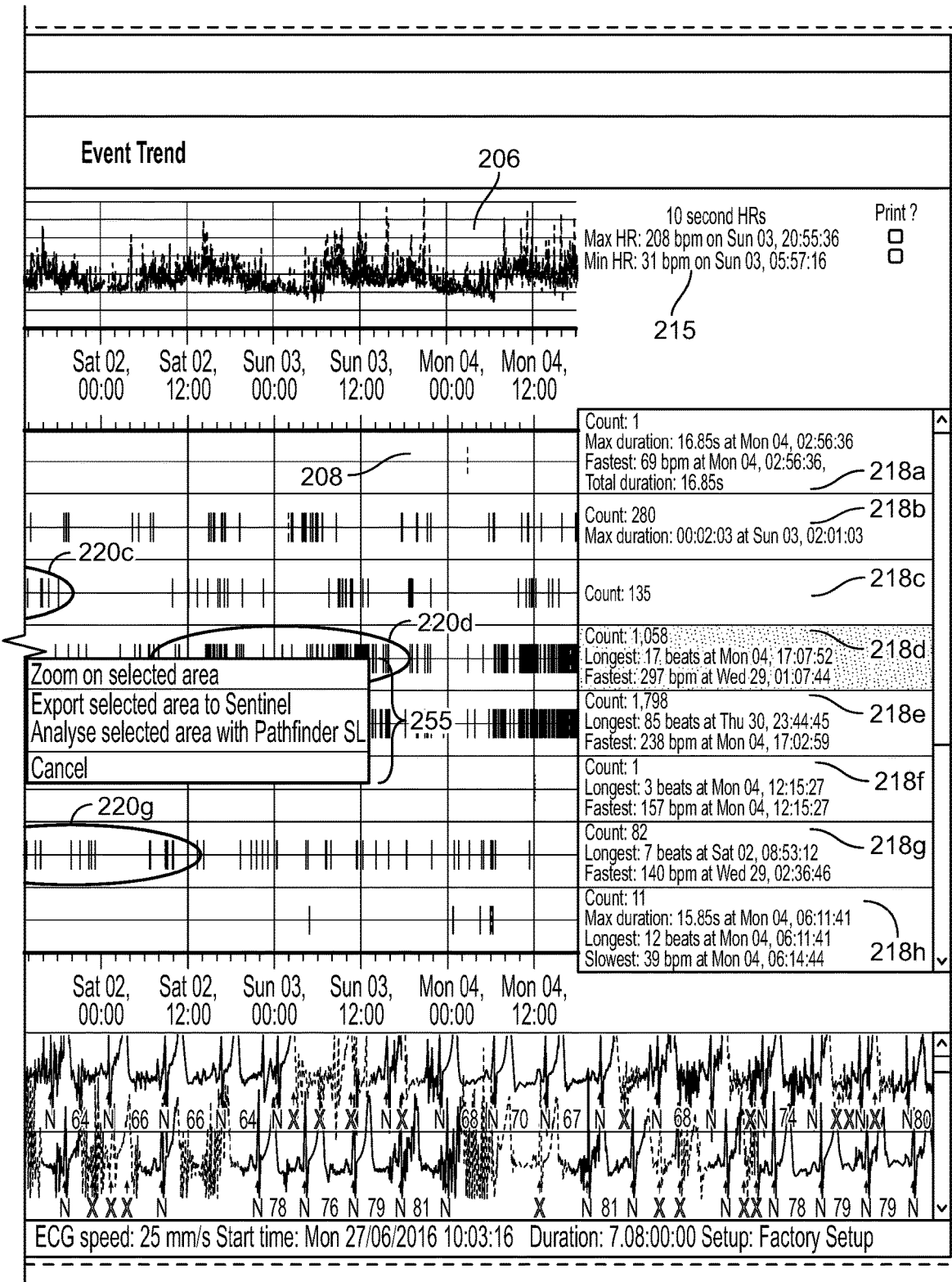

As shown in FIG. 2B, the user can select a second duration of the ECG waveform 210 or HR range 214 (from the 'pianola' display 208) encompassing a plurality of vertical lines 220d' representing occurrences of VT events in the second duration. In various embodiments, the second duration may be up to 7 days. In one embodiment, as an example, the selected second duration 225 corresponds to a period of 24 hours. In some embodiments, the user may click and drag his mouse to generate/draw an area 227 indicative of selection of the second duration and the underlying plurality of vertical lines 220$d'$ (that is, the detected VT events). In various embodiments, the area 227 may be of any suitable shape such as, but not limited to, rectangular, circular, and oval. In response to the user selecting the second duration, the ECG processing module 140 presents the user with a plurality of options 225 such as, for example, a) a first option for enabling a zoom-in function on the ECG waveform 210, HR range 214 and/or detected VT events 220$d'$ corresponding to the second duration, b) a second option to enable exporting of ECG data (corresponding to the second duration) and creating a new test, and c) a third option to enable detailed processing of ECG data (corresponding to the second duration) with reference to the second set of functionalities (comprising, as non-limiting examples, at least one of ST-analysis, QT-analysis, Heart Rate Variability-analysis, heartbeat analyses, screening of recordings for Sleep Apnea, superimposition of heartbeats. In some embodiments, the second set of functionalities is related to user-initiated reclassification of cardiac beats/morphologies and/or detected events). Depending on the user's selection, the module 140 presents a zoomed display of the ECG waveform 210, HR range 214 and/or detected VT events 220$d'$ corresponding to the second duration, exports ECG data corresponding to the second duration for creation of a new test or performs detailed processing with reference to the second set of functionalities and presents one or more outputs/results of the detailed processing to the user. In some embodiments, the new test may be created by anther module that may or may not be in data communication with the module 140. In some embodiments, the detailed processing may be performed by another module that may or may not be in data communication with the module 140. In some embodiments, when the module 140 presents a zoomed display of the ECG waveform 210, HR range 214 and/or detected VT events 220$d'$ corresponding to the second duration, the overall zoom level of the GUI screen 200 may change resulting in an upward modulation of the zoom level for heart rate in the HR range 214 as well as for other detected events in the sub-screen 208.

Figure 3:
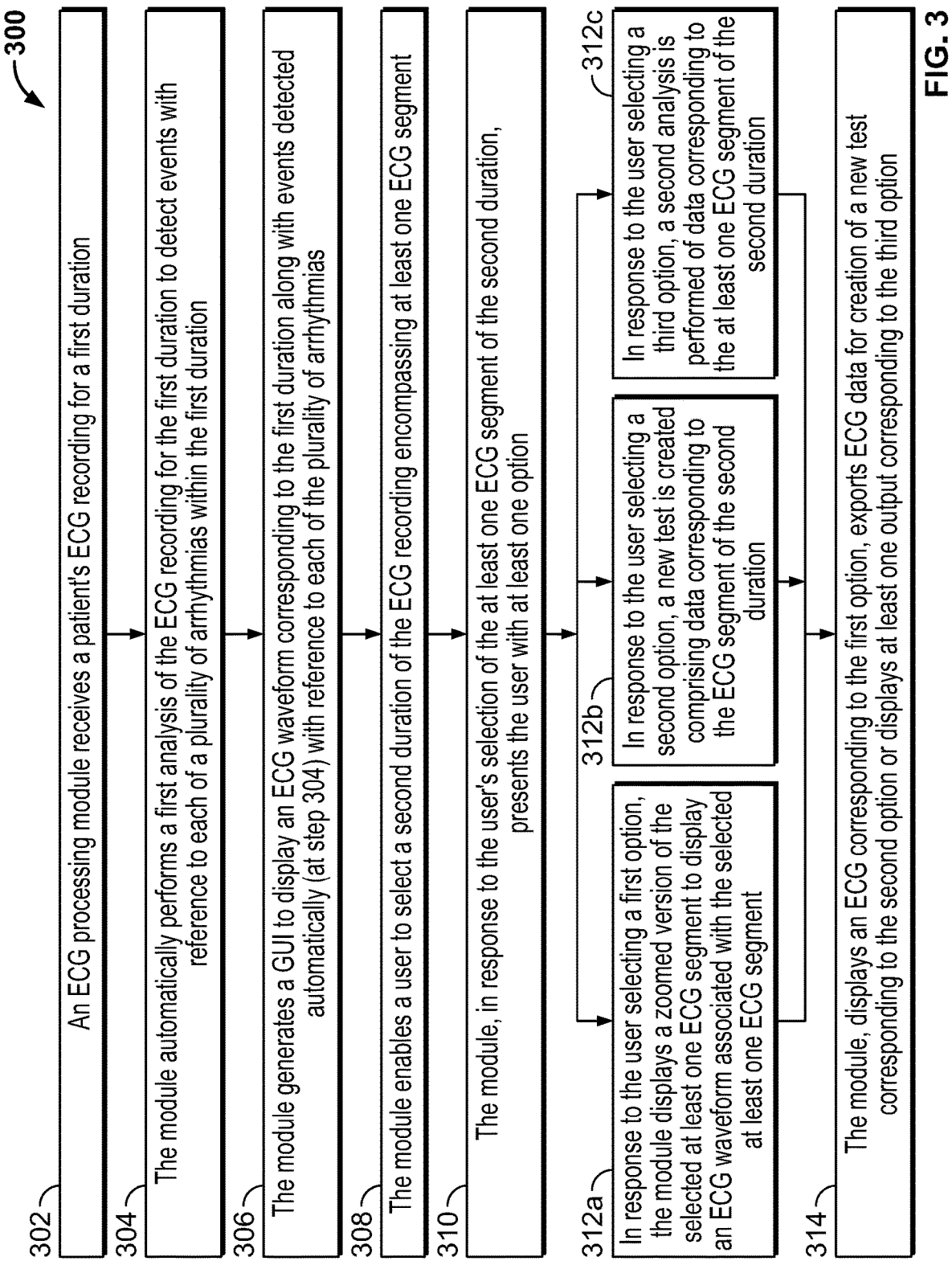
FIG. 3 is a flowchart of a method of extracting ECG data, from within a long duration ECG recording, for more detailed ECG analysis, in accordance with some embodiments of the present specification.

FIG. 3 is a flowchart of a method 300 of extracting ECG data, from within a long duration ECG recording, for more detailed ECG analysis, in accordance with some embodiments of the present specification. In embodiments, the method 300 is implemented by the ECG processing module 140 (FIG. 1). At step 302, the module 140 receives a patient's ECG recording for a first duration. At step 304, the module 140 automatically performs a first analysis of the ECG recording for the first duration to detect events with reference to each of a plurality of arrhythmias within the first duration. In embodiments, the first duration may be up to 30 days. In various embodiments, the plurality of arrhythmias comprise cardiac conditions such as, but not limited to, atrial fibrillation (AF), sinus pause or arrest, long R-R intervals, ventricular tachycardia (VT), ventricular run (V-Run), supraventricular tachycardia (SVT), supraventricular run (SV-Run), bradycardia and V-pattern including bigeminies and trigeminies.

At step 306, the module 140 generates a GUI to display an ECG waveform corresponding to the first duration along with events detected automatically (at step 304) with reference to each of the plurality of arrhythmias. In embodiments, one of a plurality of separate area, window, strip or row of the GUI is designated for each of the plurality of arrhythmias such that events detected with reference to an arrhythmia are displayed in an area designated for the arrhythmia. In some embodiments, the automatically detected events are displayed in the form of insignias such as, for example, vertical lines, dots, and icons. In some embodiments, a width or thickness of the vertical lines is indicative of duration of the detected events. In some of embodiments, a size or area of the dots or icons is indicative of duration of the detected events.

At step 308, the module 140 enables a user to select a second duration of the ECG recording encompassing at least one ECG segment in the ECG recording for the first duration. In some embodiments, the selected at least one ECG segment (of the second duration of the ECG recording) encompasses at least one significant or pathological event detected in the ECG recordings for the first duration. Stated differently, in such embodiments, the module 140 enables the user to select at least one automatically detected event thereby essentially selecting the second duration of the ECG recording that contains the at least one automatically detected event. In some embodiments, the selected at least one ECG segment (of the second duration of the ECG recording) encompasses at least one noisy (of poor quality or low signal-to-noise ratio) ECG segment in the ECG recording for the first duration.

In embodiments, the second duration may be up to 7 days. In some embodiments, a user may click and drag his mouse to generate/draw an area indicative of selection of the at least one ECG segment of the second duration. In various embodiments, the area may be of any suitable shape such as, but not limited to, rectangular, circular, and oval.

At step 310, the module 140, in response to the user's selection of the at least one ECG segment (at step 308) of the second duration, presents the user with at least one option. In some embodiments, the user is presented with a first option to enable zooming-in on the selected at least one ECG segment to display an ECG waveform associated with the selected at least one ECG segment, a second option to enable exporting of ECG data corresponding to the second duration and subsequently creating a new test and a third option to enable performing a second analysis of the data corresponding to the ECG segment of the second duration.

At step 312$a$, in response to the user selecting the first option, the module 140 displays a zoomed version of the selected at least one ECG segment to display an ECG waveform associated with the selected at least one ECG segment.

At step 312$b$, in response to the user selecting the second option, the module 140 enables a new test to be created comprising data corresponding to the at least one ECG segment (selected at step 308) of the second duration. In some embodiments, the data is exported to a first module (which may be in data communication with the module 140) for creation of the new test. In some embodiments, the first module is a standalone module separate from the module 140.

At step 312$c$, in response to the user selecting a third option, the module 140 calls upon a second module configured to perform a second analysis of data corresponding to the at least one ECG segment (selected at step 308) of the second duration. In various embodiments, the second analysis may be performed immediately or later when required. In some embodiments, the second module is a standalone module separate from the module 140 and in data communication with the module 140.

In some embodiments, the second analysis entails more detailed assessment of the ECG segment of the second duration compared to the first analysis. In some embodiments, the second analysis comprises, as non-limiting examples, at least one of ST-analysis, QT-analysis, Heart Rate Variability-analysis, heartbeat analyses, screening of recordings for Sleep Apnea, superimposition of heartbeats. In some embodiments, the second analysis is related to the user-initiated reclassification of cardiac beats/morphologies and/or detected events.

At step 314, the module 140 displays an ECG corresponding to the first option, exports ECG data for creation of a new test corresponding to the second option or displays at least one analysis corresponding to the third option. In some embodiments, the new test corresponding to the second option is created by the first module. In alternate embodiments, the at least one analysis corresponding to the third option may be displayed or rendered on the at least one display 122 (FIG. 1) by the second module.

In accordance with some aspects of the present specification, the ECG processing module 140 (FIG. 1) executes a plurality of sequences of programmatic instructions or code to enable or cause at least one CPU of the computing device 120 to generate a GUI that displays ECG waveform segments corresponding to detected events within a sub-screen, window, area or portion designated for each of the various categories of cardiac arrhythmias. In embodiments, the module 140 dynamically displays counts of the number of detected events for each category of cardiac arrhythmia and populates each category with ECG waveform segments associated with the detected events—as the module 140 analyses the ECG recordings.

In some embodiments, presentation of ECG waveform segments within each category of cardiac arrhythmia are ordered in terms of highest (clinical) severity first (that is, in a descending order of severity), so the user always sees the most clinically severe event at the top of that category. In some embodiments, each category of cardiac arrhythmia is populated with up to 'n', say 10, events (in cases where the module 140 detects more than 'n' events for a category of arrhythmia). In embodiments, contents of each category is automatically updated with a next most severe event should the user delete a detected event from a category or re-classify a detected event away from the category of arrhythmia.

Figure 4A:
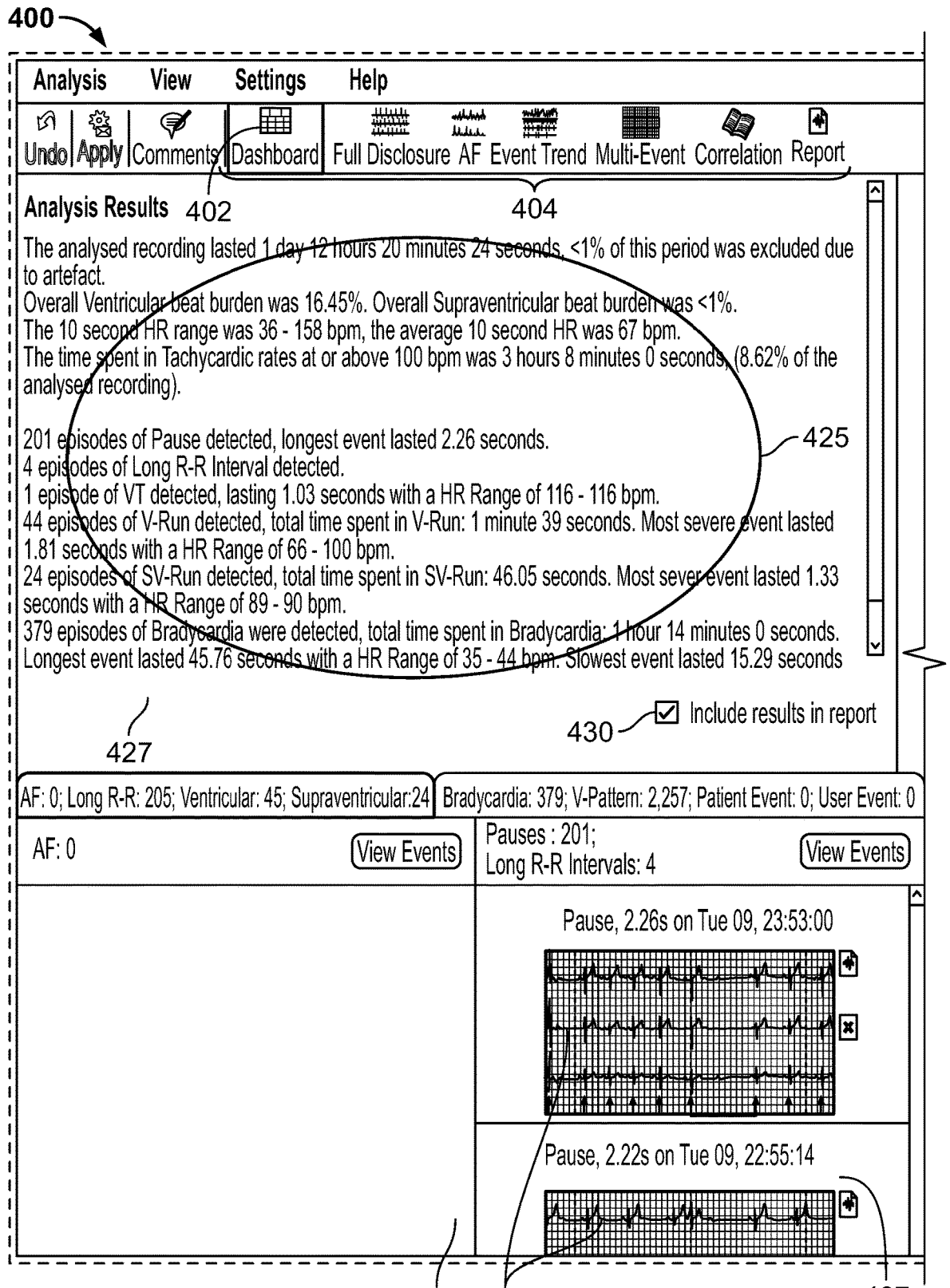
FIG. 4A shows a GUI screen configured to display a first plurality of results of ECG analyses, in accordance with some embodiments of the present specification.
Figure 4A:
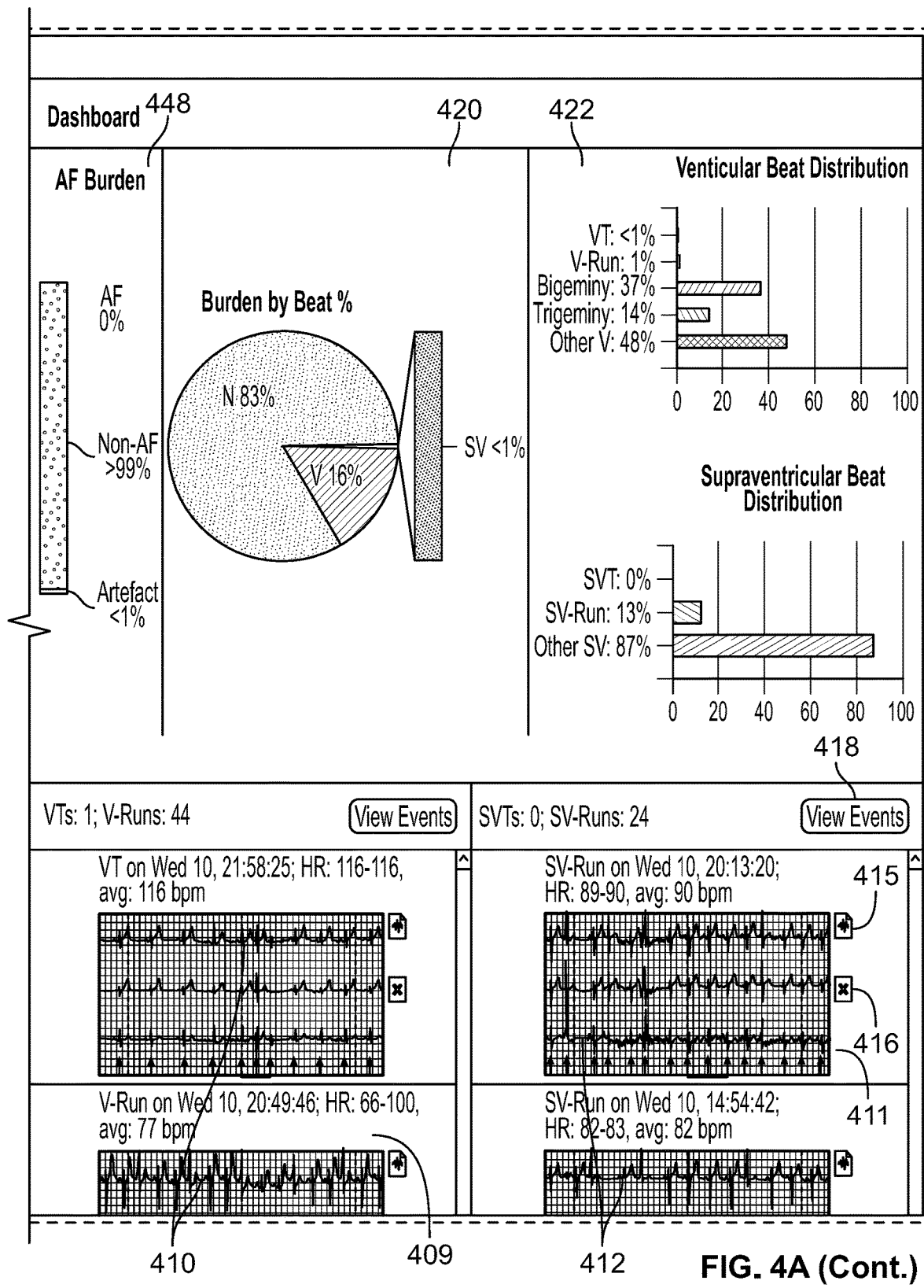
Figure 4B:
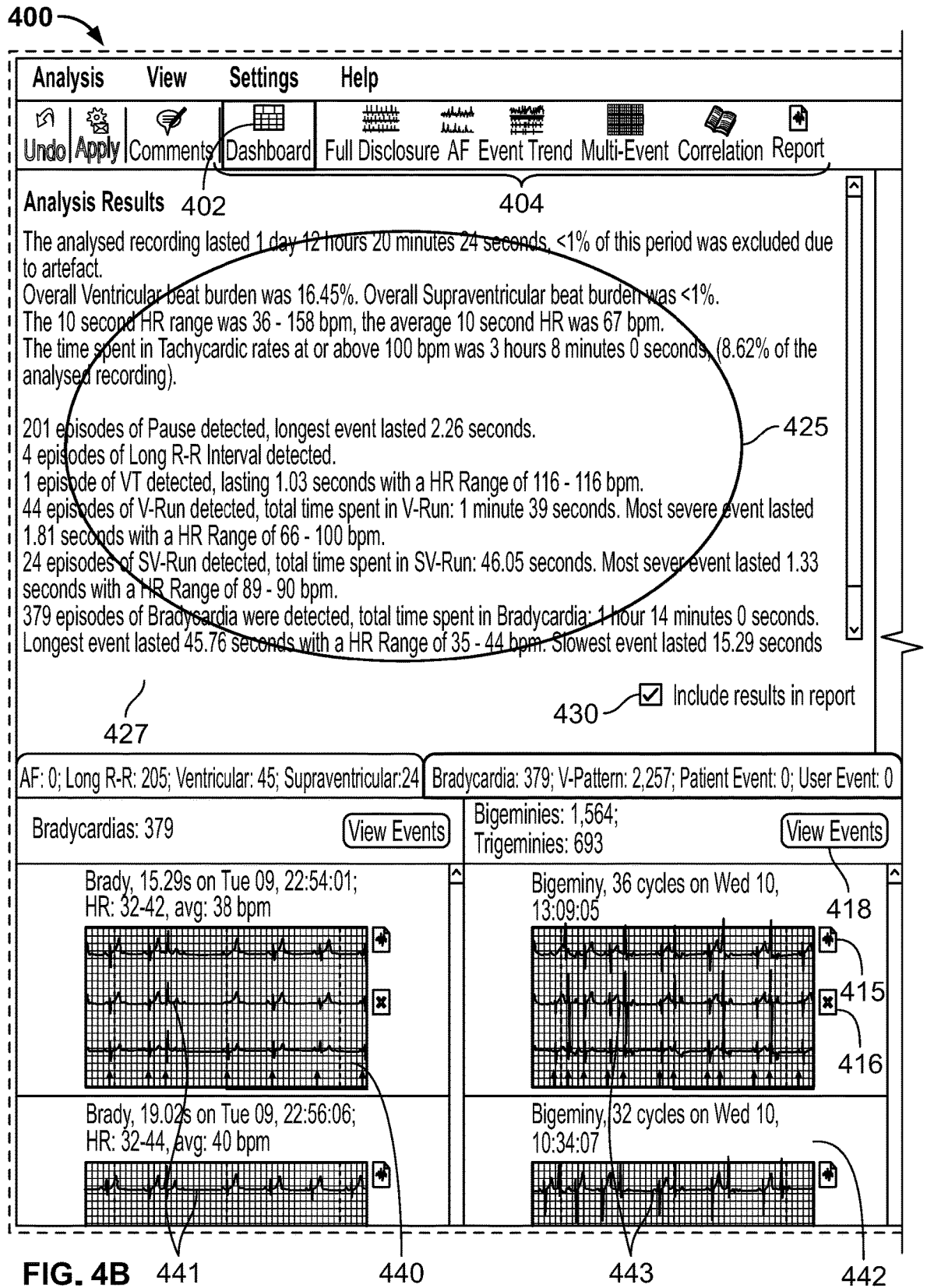
FIG. 4B shows the GUI screen of FIG. 4A configured to display a second plurality of results of ECG analyses, in accordance with some embodiments of the present specification.
Figure 4B:
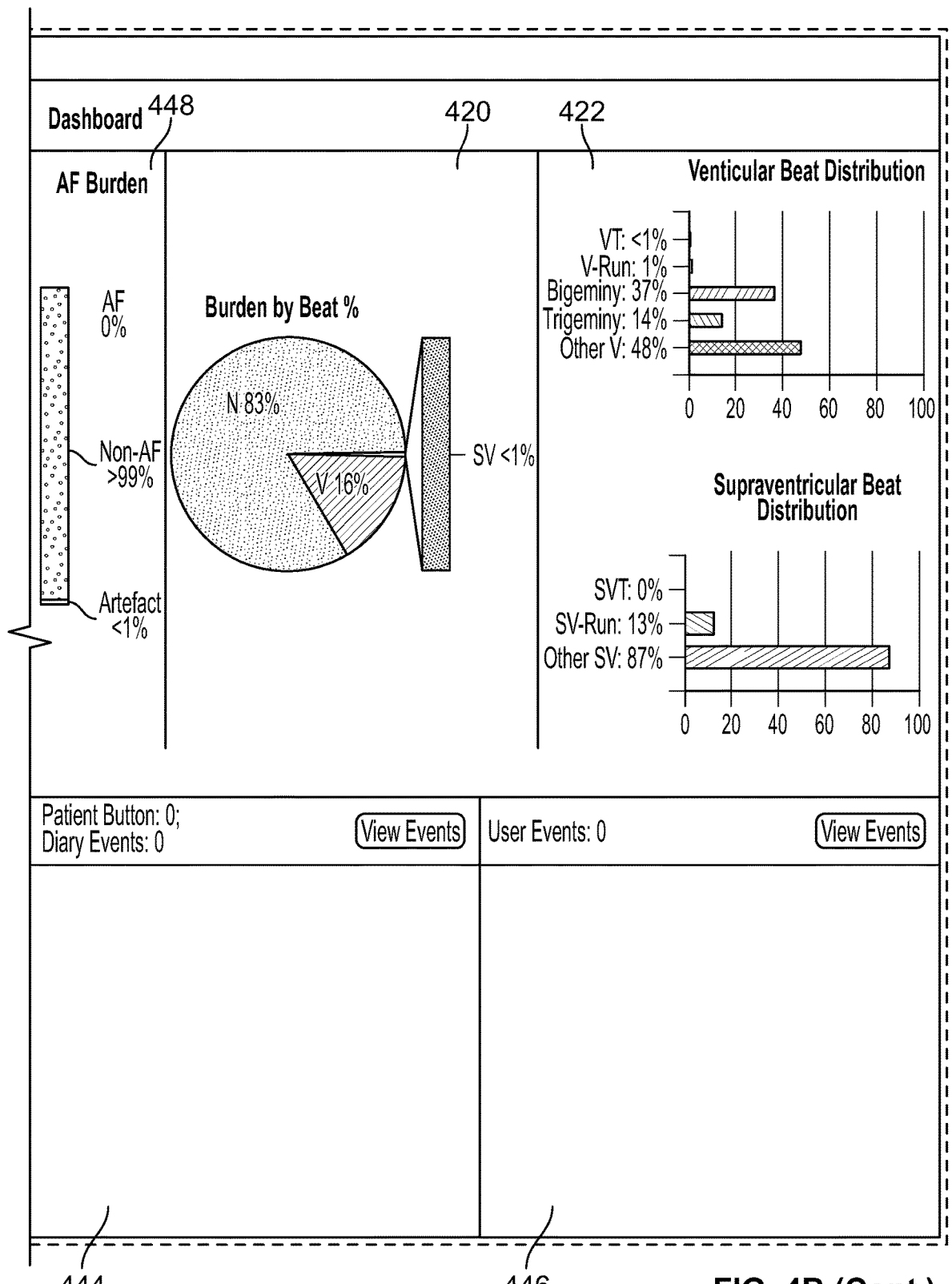

Referring now to FIGS. 4A and 4B, the ECG processing module 140 (FIG. 1) generates a GUI screen 400 in response to the user clicking a dashboard icon or button 402 displayed on the main menu 404. In some embodiments, the GUI screen 400 is a composite interface having one sub-screen, window, area or section for each of the various categories of cardiac arrhythmia. In accordance with one embodiment, the screen 400, for example, illustrates a first sub-screen 405 for atrial fibrillation (AF) as a first category of arrhythmias, a second sub-screen 407 for pauses and long R-R intervals as a second category of arrhythmias, a third sub-screen 409 for ventricular tachycardia (VT) and ventricular run (V-run) as a third category of arrhythmias, a fourth sub-screen 411 for supraventricular tachycardia (SVT) and supraventricular run (SV-run) as a fourth category of arrhythmias, a fifth sub-screen 440 for bradycardia as a fifth category of arrhythmias, a sixth sub-screen 442 for V-pattern (including bigeminies and trigeminies) as a sixth category of arrhythmias, a seventh sub-screen 444 for displaying one or more patient-recorded events and an eighth sub-screen 446 for displaying one or more user events As shown, each sub-screen further displays a count of the events detected for the category of arrhythmias associated with the sub-screen and are also populated with ECG waveform segments of the events detected in the category. For example, the first sub-screen 405 displays AF count as zero and is therefore not populated with any ECG waveform segments since no AF events were detected. The second sub-screen 407 displays counts for pauses and long R-R intervals as 201, 4 respectively. The sub-screen 407 is also populated with date and time stamped ECG waveform segments 408 corresponding to top 'n' most severe or significant detected pauses in a descending order of severity. The third sub-screen 409 displays counts for VTs and VT-runs as 1, 44 respectively. The sub-screen 409 is also populated with date and time stamped ECG waveform segments 410 corresponding to the detected VTs and VT-runs. The fourth sub-screen 411 displays counts for SVTs and SV-runs as 0, 24 respectively. The sub-screen 411 is also populated with date and time stamped ECG waveform segments 412 corresponding to top 'n' most severe or significant detected SV-runs in a descending order of severity. The fifth sub-screen 440 displays counts for bradycardia events as 379. The sub-screen 440 is also populated with date and time stamped ECG waveform segments 441 corresponding to top 'n' most severe or significant detected bradycardia events. The sixth sub-screen 442 displays a count for bigeminies (1564, in an embodiment) and a count for trigeminies (692, in an embodiment). The sub-screen 442 is also populated with date and time stamped ECG waveform segments 443 corresponding to top 'n' most severe or significant detected bigeminy and/or trigeminy events. The seventh and eighth sub-screens 444, 446 display counts for patient-recorded events and user events as 0, 0 respectively.

Figure 9A:
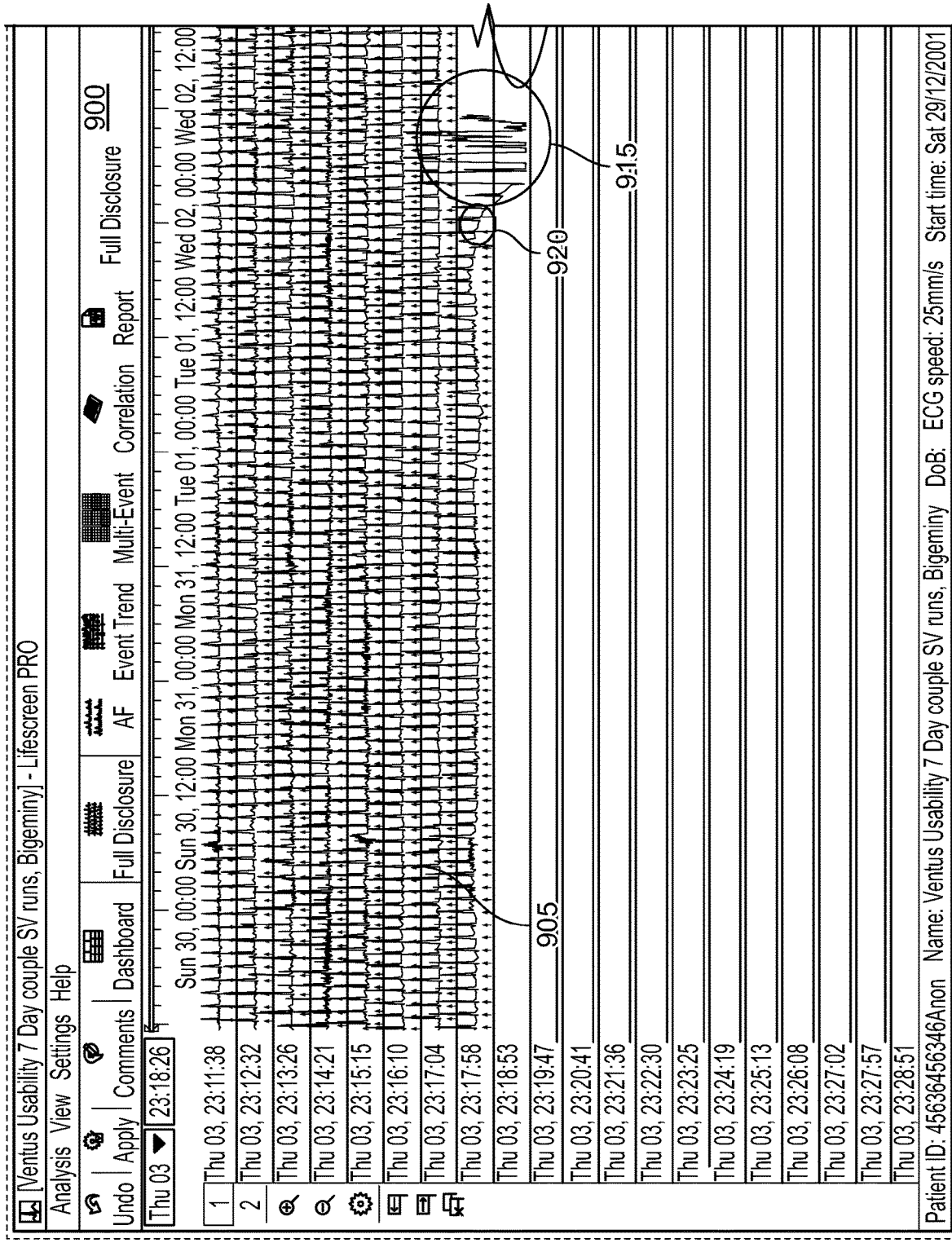
FIG. 9A shows a GUI highlighting an automatically determined end of ECG analysis point, in accordance with some embodiments of the present specification.
Figure 9A:
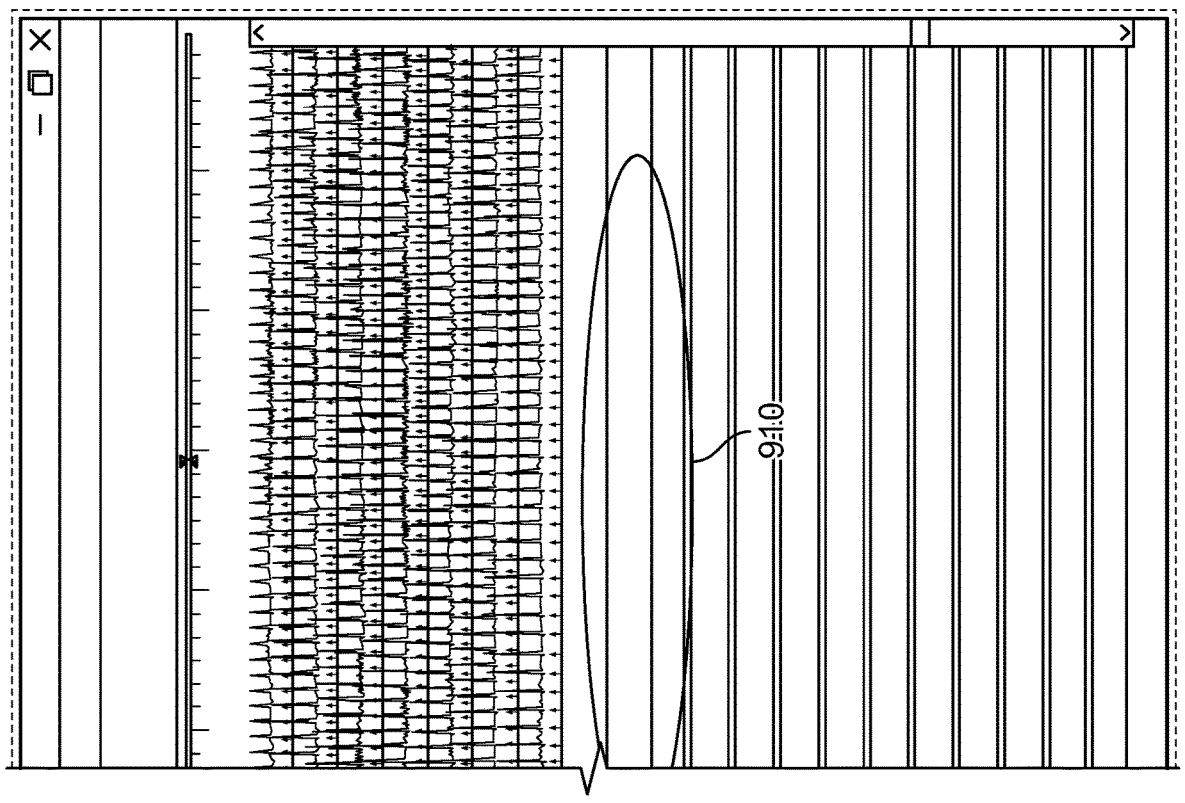
Figure 9B:
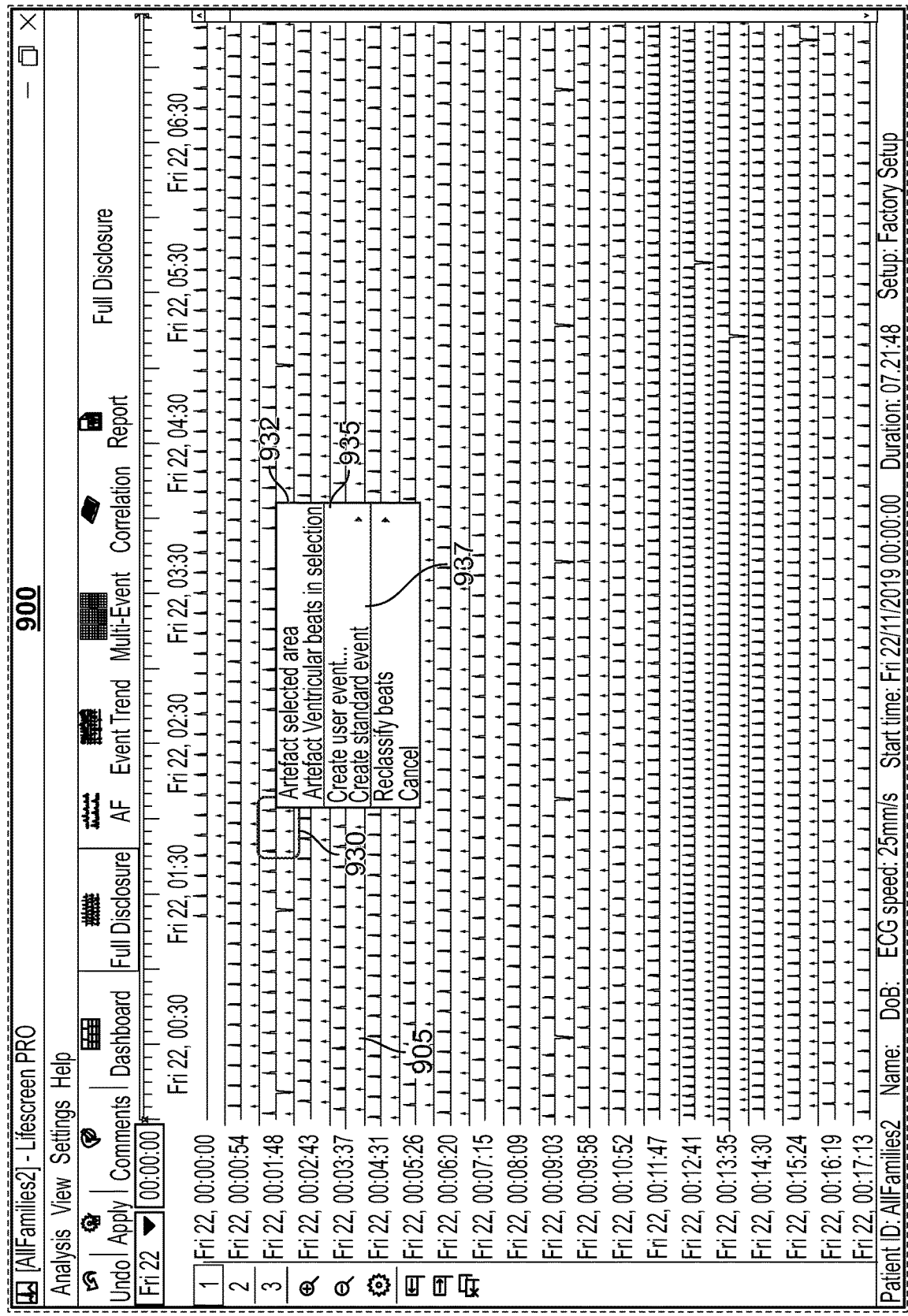
FIG. 9B illustrates a first step of selecting and defining an ECG segment as a user event, in accordance with some embodiments of the present specification.
Figure 9C:
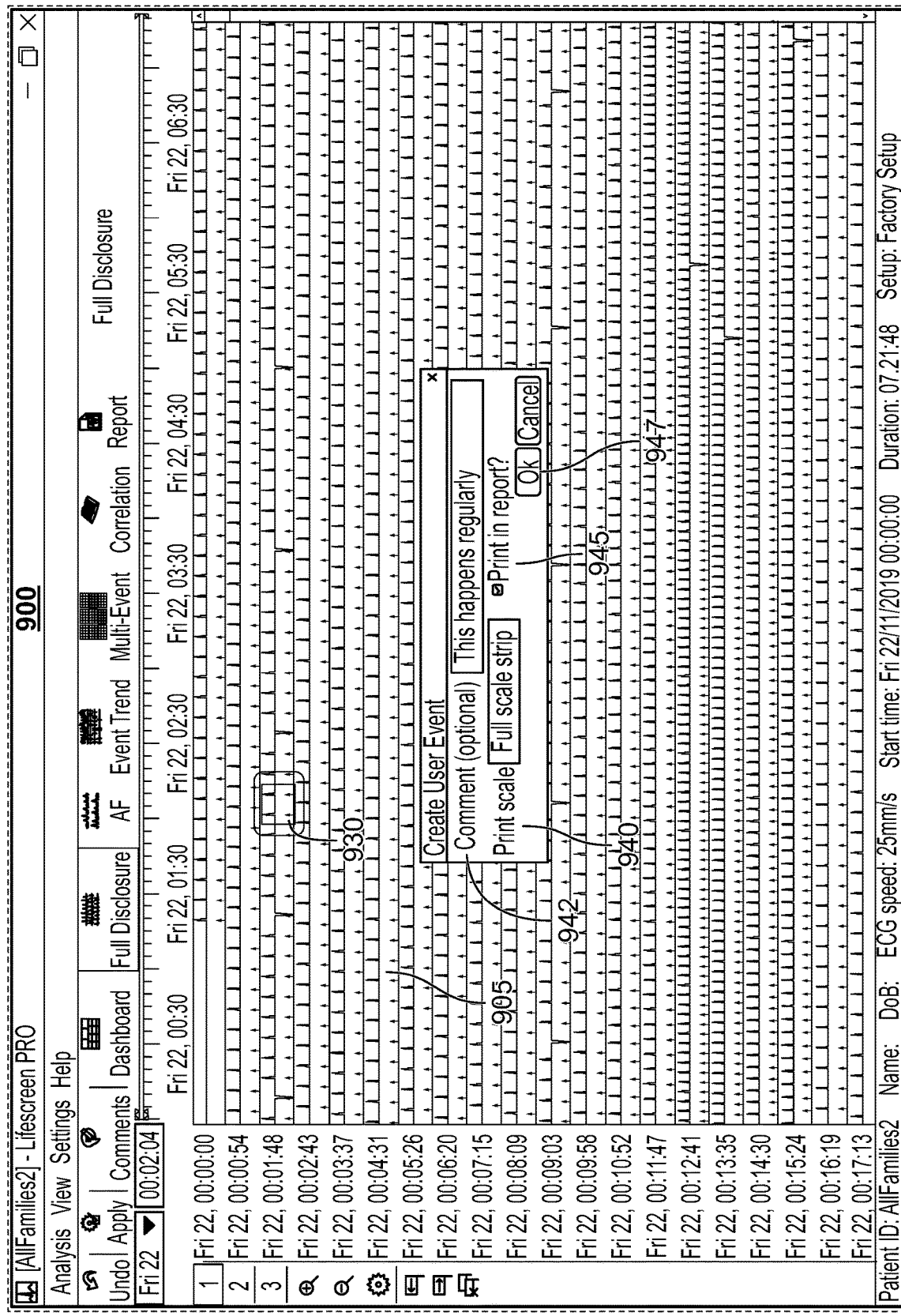
FIG. 9C illustrates a second step of selecting and defining an ECG segment as a user event, in accordance with some embodiments of the present specification.

In embodiments, a user can select one or more segments from an ECG waveform, such as an ECG waveform 905 of FIG. 9B, and manually mark the selected one or more segments as ECG events. When marking a selected ECG segment as an event, the user may define whether that ECG event is a 'standard event' (such as, for example, an AF event, a Pause event or a Long R-R Interval) or whether that ECG event is a 'user event'. As illustrated in FIG. 9B, the user may select a segment 930, and click on the selected segment 930 to open a window 932 of options. The window 932 lists at least a first option 935 to create or define the segment 930 as a 'user event' and a second option 937 to create or define the segment 930 as a 'standard event'. As illustrated in FIG. 9C, if the user selects the first option 935, a dialog box 940 is generated that allows the user to add a comment 942 (to be associated with the 'user event') and enables/disables a checkbox 945 to include/not-include the 'user event' in an ECG report. Upon clicking the 'ok' button 947, the segment 930 is defined and saved as the 'user event'.

Referring back to FIGS. 4A, 4B, defining a 'standard event' results in a count associated with that type of event increasing by 1 in a sub-screen associated with the 'standard event' (as shown, for example, in the sub-screens 405, 407, 409, 411, 440, 442). It also results in an ECG waveform segment of the 'standard event' being added to the sub-screen associated with the 'standard event'. On the other hand, 'user events' are typically segments of ECG that are or may be of interest to a reviewing physician since these segments may show some anomaly, repetition, or pattern that is not a standard event, but is something to be considered when reviewing the patient's ECG. New analyses have zero 'user events' (as shown in the eighth sub-screen 446) since these are only created or user-defined. In embodiments, each new 'user event' created/defined results in a date and time stamped ECG segment, corresponding to the new 'user event', being added to the sub-screen 446. In embodiments, the user is enabled to create as many 'user events' as he wants (while displaying ECG segments of only the top 'n' most severe or significant 'user events'), and he can further choose which 'user event(s)' get included in an ECG analysis report.

The print and delete icons or buttons 415, 416 displayed next to each ECG waveform segment in a category enable the user to either mark (or print) that ECG waveform segment for inclusion within an ECG analysis report or delete that auto-detected event from the analysis. The view events icon or button 418 enables the user to review all events detected in a category in situations where there are a large number of detected events (greater than 'n') in the category.

In embodiments, if the user clicks on (thereby selecting) any one of the displayed ECG waveform segments within the sub-screens 405 (no ECG waveform segment displayed in this embodiment), 407, 409, 411, 440, 442, 444 and 446 the module 140 generates and presents (within another GUI on the same display monitor used to show the GUI 400 or on another display monitor configured for this purpose) a composite ECG waveform comprising of the selected ECG waveform segment along with a predetermined duration of ECG waveforms before and after the selected ECG waveform segment. This provides the user with more context of what happened in the ECG recording both before and after the selected or clicked ECG waveform segment (or the associated event).

The GUI screen 400 further illustrates a ninth sub-screen 420 that presents a graphical representation of burden by beat percentage, a tenth sub-screen 422 that presents a first graphical representation of ventricular beats, a second graphical representation of supraventricular beats and an eleventh sub-screen 448 that presents a graphical representation of atrial fibrillation burden.

In accordance with some aspects of the present specification, the ECG processing module 140 also automatically generates textual annotation, information or comments 425 that provide the user with a descriptive overview of the findings of the module 140 as a result of analyses of the ECG recordings for the first duration. In some embodiments, the textual information 425 is presented in a twelfth sub-screen 427. In embodiments, the contents of the textual information 425 are dynamically updated if the user edits (for example, re-classifies a detected event) and/or deletes one or more events detected by the module 140. If the user selects the option button 430, the textual annotation is directly included within an ECG analysis report.

Figure 5A:
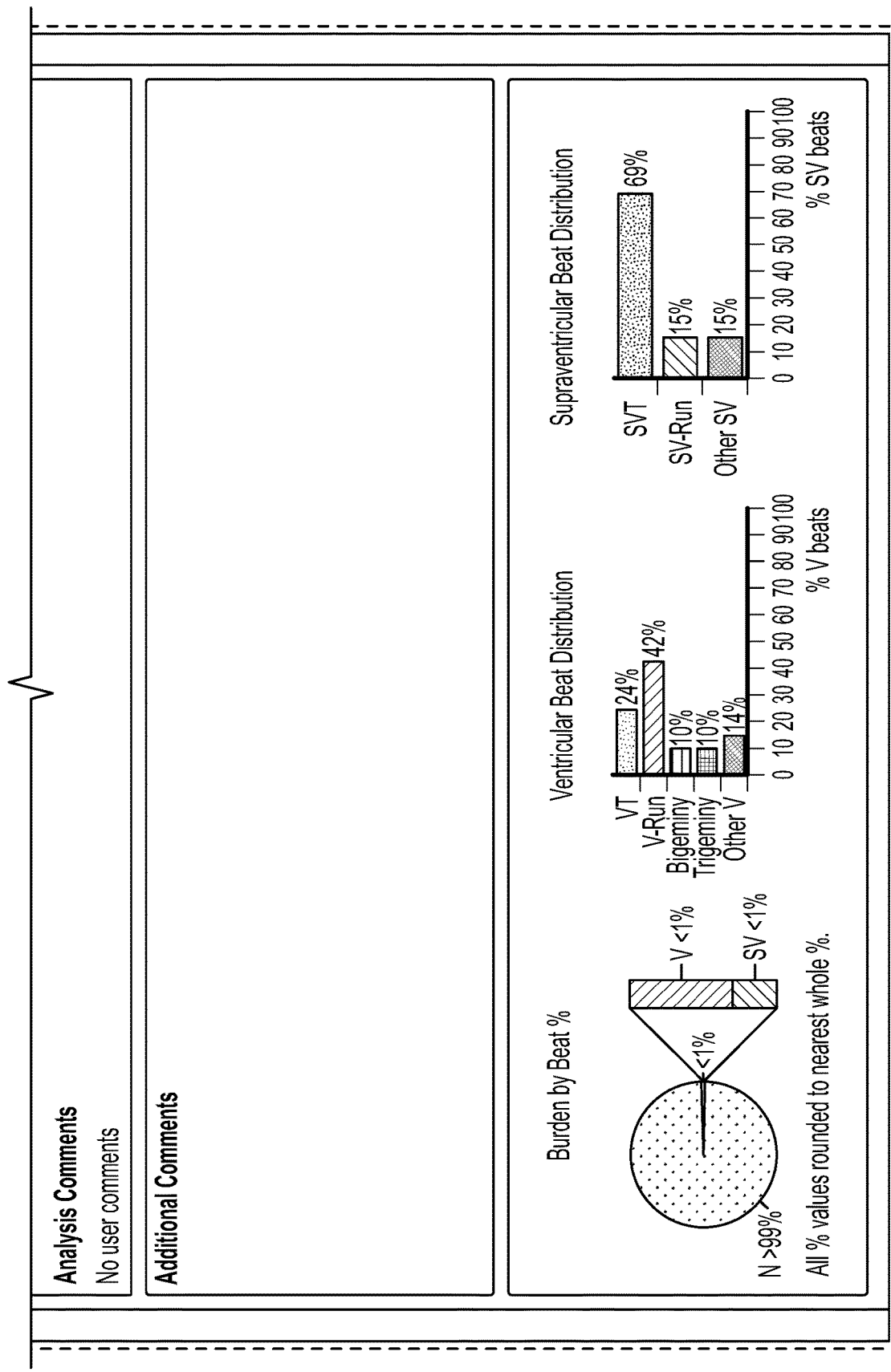
FIG. 5A shows an ECG analysis report with auto-generated textual information being included, in accordance with some embodiments of the present specification.
Figure 5B:
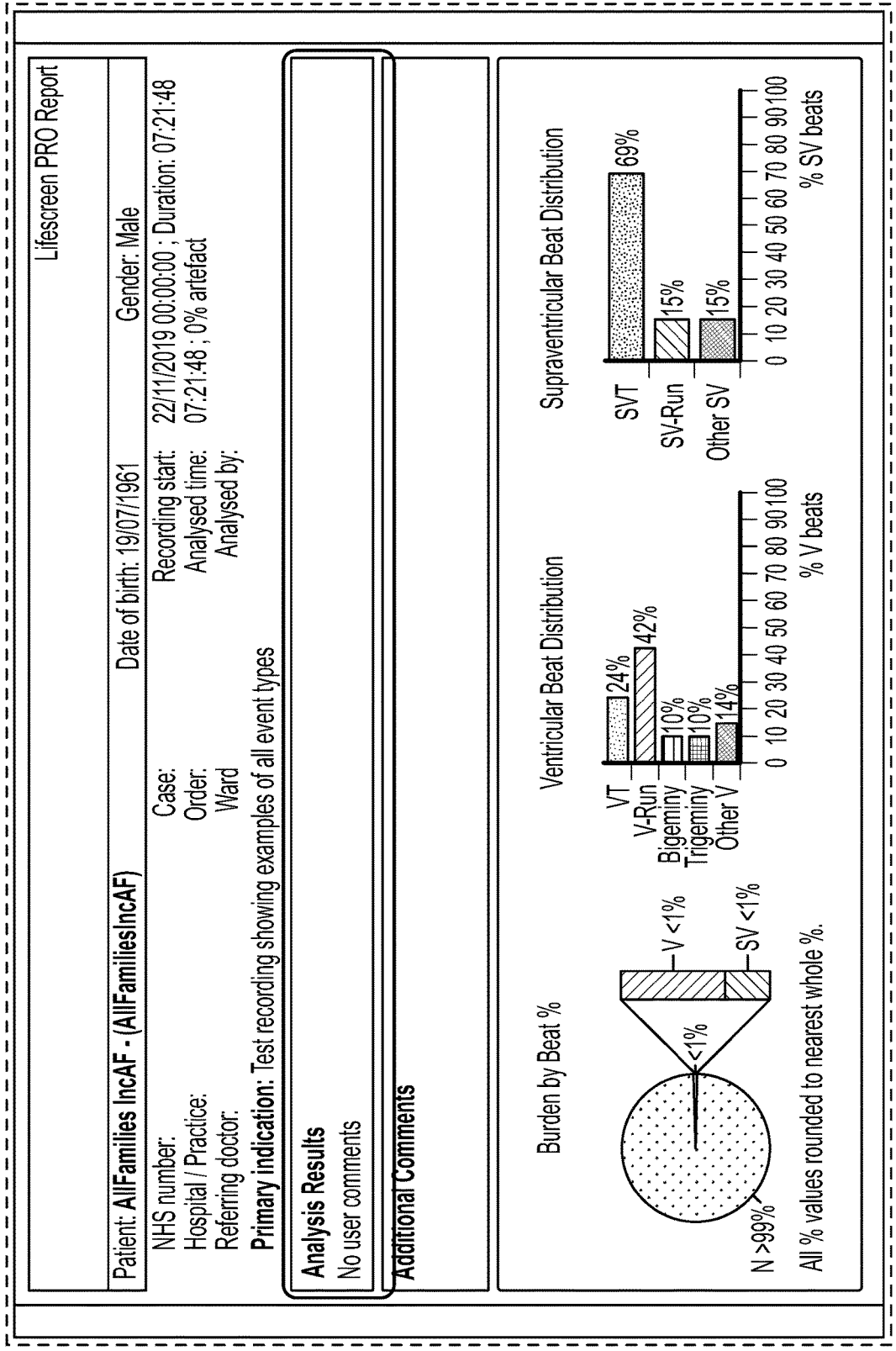
FIG. 5B shows an ECG analysis report with auto-generated textual information not included, in accordance with some embodiments of the present specification.
Figure 5C:
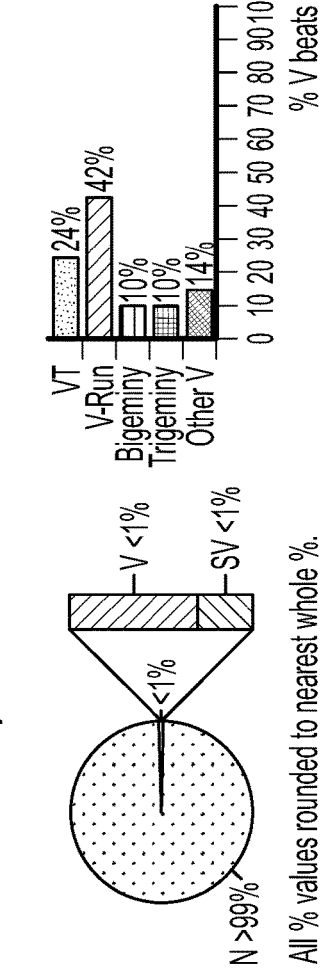
FIG. 5C shows an ECG analysis report with auto-generated textual information being included with edits, in accordance with some embodiments of the present specification.
Figure 5C:
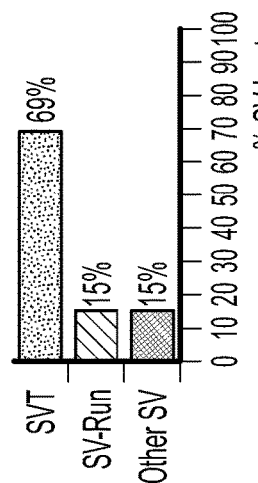

As shown in FIG. 5A, the user may include the textual information 425 (FIGS. 4A, 4B) directly into an ECG analysis report 505a. Alternatively, as shown in FIG. 5B, the user may choose not to include the textual information 425 (FIGS. 4A, 4B) into an ECG analysis report 505b. Still alternatively, as shown in FIG. 5C, the user may choose to copy and edit the textual information 425 (FIGS. 4A, 4B) for inclusion (as edited information 425') within an ECG analysis report 505c or the user may include the textual information 425 in the ECG analysis report 505c for subsequent editing (as edited information 425'). Thus, the user has options to use, omit or re-use the textual information 425 (within an ECG analysis report) auto-generated by the module 140.

Figure 6A:
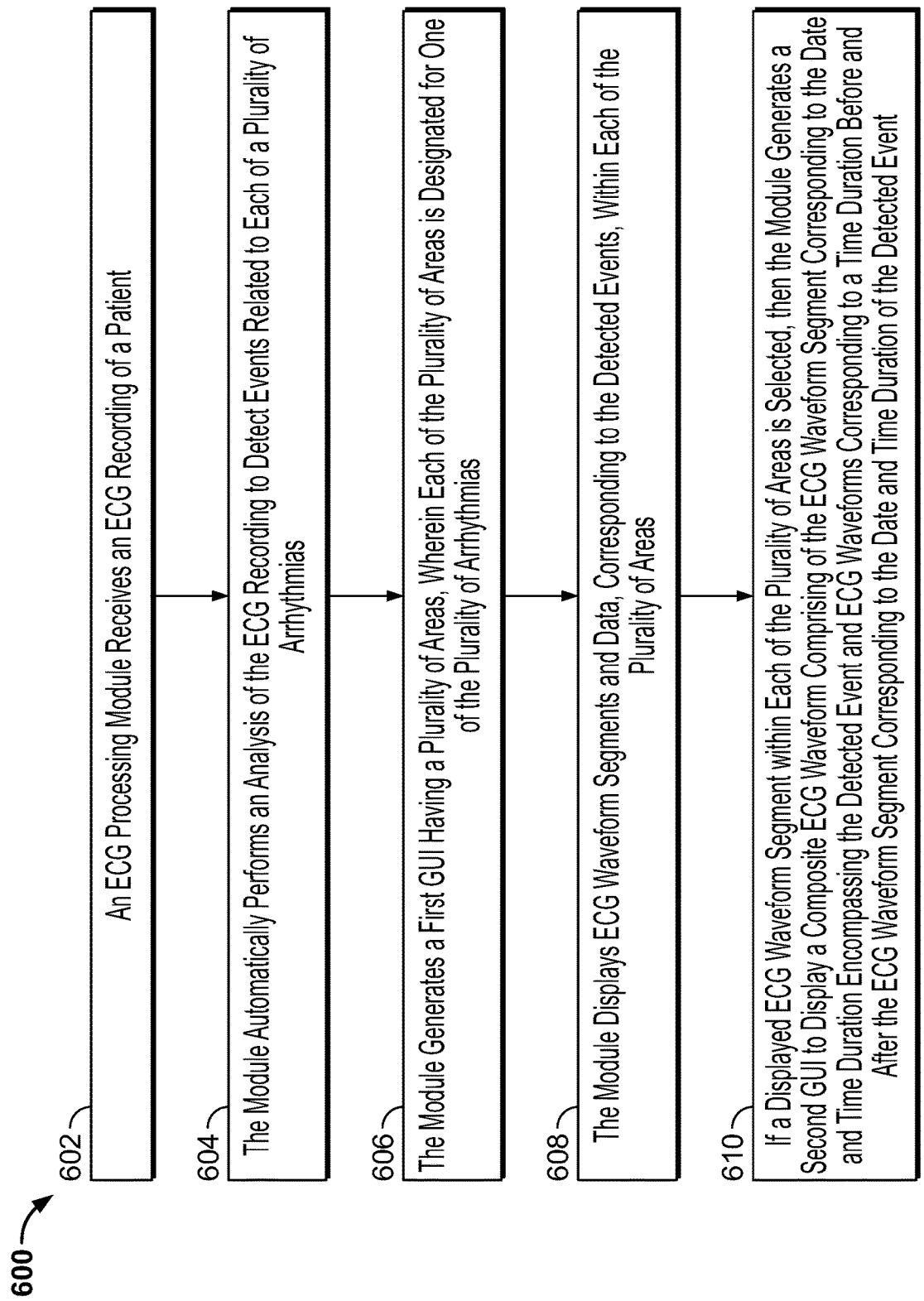
FIG. 6A is a flowchart of a method of displaying detected arrhythmia events, in accordance with some embodiments of the present specification.

FIG. 6A is a flowchart of a method 600 of displaying detected arrhythmia events, in accordance with some embodiments of the present specification. In embodiments, the method 600 is implemented by the ECG processing module 140 (FIG. 1). At step 602, the module 140 receives an ECG recording of a patient. At step 604, the module 140 automatically performs an analysis of the ECG recording to detect events related to each of a plurality of arrhythmias such as, but not limited to, atrial fibrillation (AF), sinus pause or arrest, Long RR-intervals, ventricular tachycardia (VT), ventricular run (V-Run), supraventricular tachycardia (SVT), supraventricular run (SV-Run), bradycardia and V-pattern including bigeminies and trigeminies.

At step 606, the module 140 generates a first GUI having a plurality of areas, sub-screens, windows or sections. In some embodiments, each of the plurality of areas is designated for one of the plurality of arrhythmias. At step 608, the module 140 displays ECG waveform segments and data, corresponding to the detected events, within each of the plurality of areas. In some embodiments, the data corresponding to the detected events includes a count of the total number of detected events for each of the plurality of areas. In various embodiments, time duration of the ECG waveform segments (corresponding to the detected events) being displayed depends at least upon a zoom level chosen by the user and a size of the user's display monitor.

In some embodiments, the ECG waveform segments within each of the plurality of areas are ordered in a descending order of severity of the corresponding detected events. In embodiments, each of the plurality of areas displays up to 'n' number of ECG waveform segments. In some embodiments, 'n'=10. In some embodiments, each of the plurality of areas is updated with an ECG waveform segment corresponding to a next most severe detected event if a displayed ECG waveform segment in the area is deleted or re-classified by a user.

If a displayed ECG waveform segment within each of the plurality of areas is selected or clicked upon then, at step 610, the module 140 generates a second GUI to display a composite ECG waveform comprising of the ECG waveform segment corresponding to the date and time duration encompassing the detected event and ECG waveforms corresponding to a time duration before and after the ECG waveform segment corresponding to the date and time duration of the detected event. In various embodiments, the time duration of the ECG waveform segments being displayed depends at least upon a zoom level chosen by the chosen and a size of the user's display monitor. In some embodiments, the module 140 displays the composite ECG waveform on a second display screen/monitor configured to display the generated second GUI.

Figure 6B:
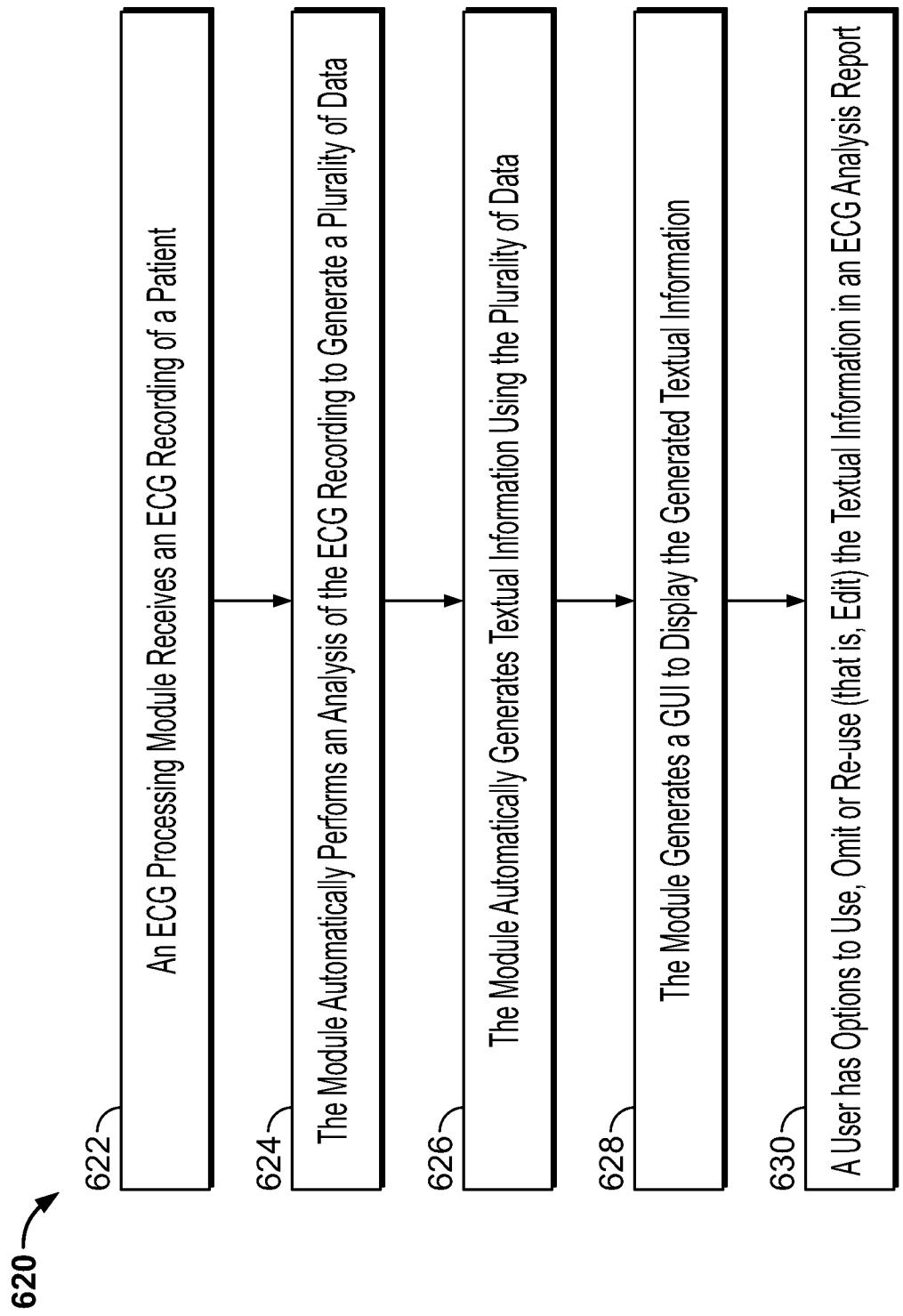
FIG. 6B is a flowchart of a method of generating and displaying textual information related to detected arrhythmia events, in accordance with some embodiments of the present specification.

FIG. 6B is a flowchart of a method 620 of generating and displaying textual information related to detected arrhythmia events, in accordance with some embodiments of the present specification. In embodiments, the method 620 is implemented by the ECG processing module 140 (FIG. 1). At step 622, the module 140 receives an ECG recording of a patient. At step 624, the module 140 automatically performs an analysis of the ECG recording to generate a plurality of data. In various embodiments, the plurality of data comprises, for example, one or more of: total time duration of the ECG recording analyzed, percentage of the total time duration excluded due to artifact (such as, for example, noise signals), ventricular beat burden, supraventricular beat burden, count of events detected for each of a plurality of arrhythmias, and one or more statistics related to the events detected for each of the plurality of arrhythmias. Non-limiting examples of the statistics include: a longest pause amongst detected pauses, total time spent in V-run and the time duration for which a longest V-run lasted, total time spent in SVT and duration of a longest SVT event, total time spent in bradycardia, duration of longest and slowest bradycardia event and heart rate ranges for one or more detected events.

At step 626, the module 140 automatically generates textual information using the plurality of data. At step 628, the module 140 generates a GUI to display the generated textual information. In some embodiments, the textual information is displayed in an area designated for the textual information within the GUI. In some embodiments, the displayed textual information is dynamically updated if one or more detected events are deleted or re-classified by a user.

At step 630, in some embodiments, upon selection of an option within the GUI, the textual information can be included in an ECG analysis report. In some embodiments, the included textual information can be edited in the ECG analysis report. In some embodiments, upon non-selection of an option within the GUI, the textual information is omitted from inclusion in an ECG analysis report.

In accordance with some aspects of the present specification, the ECG processing module 140 (FIG. 1) executes a plurality of sequences of programmatic instructions or code to enable or cause at least one CPU of the computing device 120 to generate a GUI that displays patient-recorded events along with automatically detected arrhythmia events for a period of time before and after the patient-recorded events.

Patient events are instances where the patient has typically experienced a symptom such as, for example, shortness of breath, tight chest, faintness, and dizziness. In some embodiments, a patient records or logs these symptomatic instances or events using an ECG recording device (device 115 of FIG. 1) such as by, for example, actuating a button on the ECG recording device. Actuating the button causes the ECG recording device to record a date and time stamped patient event. In some embodiments, the patient keeps a record of these symptomatic instances or events using a paper diary that his submitted for analysis along with the ECG recording device. In some embodiments, the patient events recorded in the paper diary are inputted into the computing device 120 for processing by the module 140.

Figure 7:
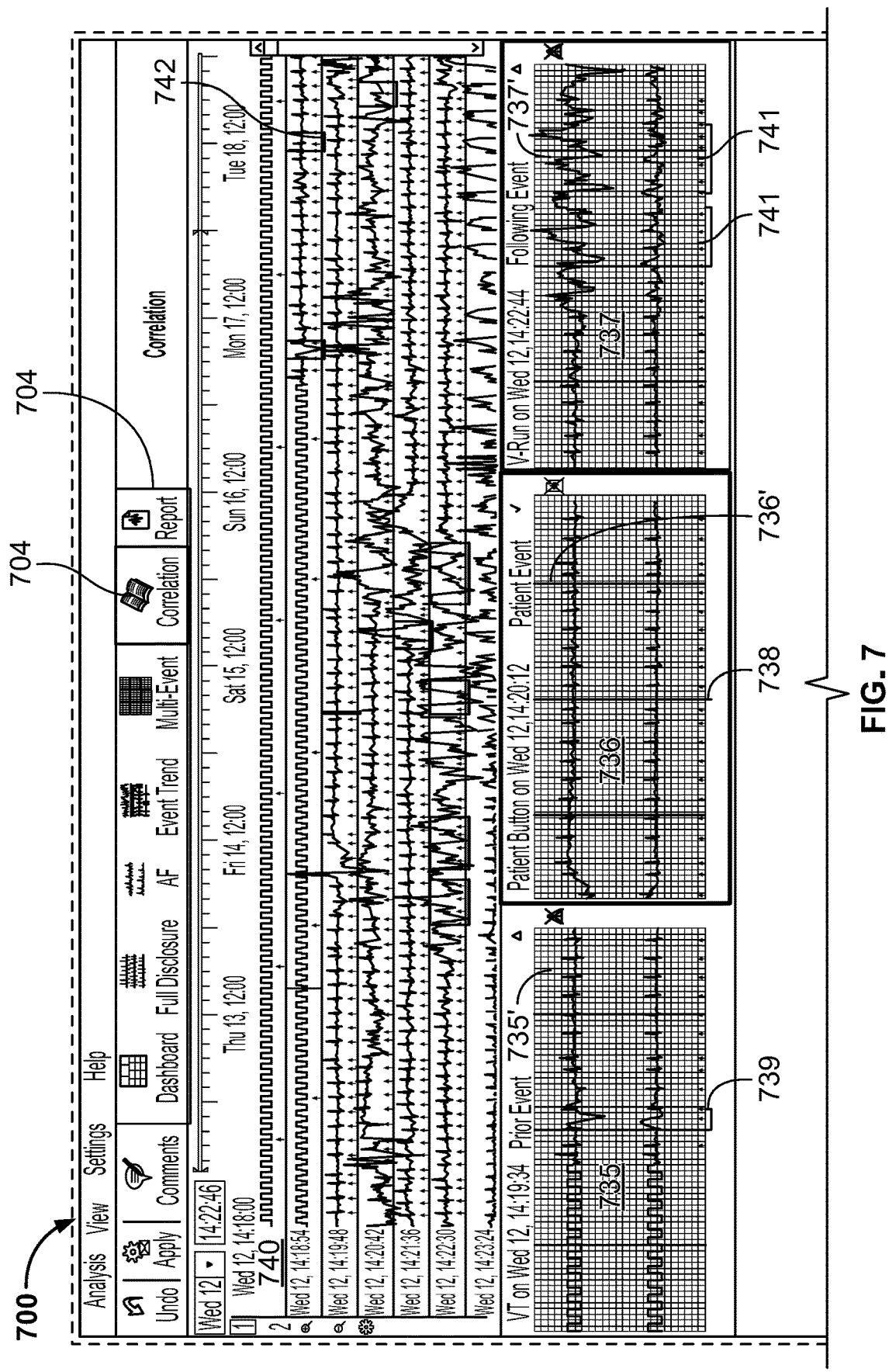
FIG. 7 shows a GUI to display automatically detected events in correlation with patient-recorded events, in accordance with some embodiments of the present specification.

Referring now to FIG. 7, the ECG processing module 140 generates a GUI screen 700 in response to the user clicking a correlation icon or button 702 displayed on the main menu 704. In some embodiments, the GUI screen 700 is a composite interface having a first sub-screen 710 that displays all date and time stamped patient-recorded symptomatic events, such as event 712. In some embodiments, the patient-recorded symptomatic events are presented in a tabular format 745 including columns such as, for example, a first column 714 for enabling the user to correlate the patient-recorded event 712 with one or more auto-detected arrhythmia events before and/or after the patient-recorded event 712. The first column 714 displays a checkbox for each of the auto-detected arrhythmia events being displayed on the first column 714. The tabular format 745 further includes a second column 716 for an event type (such as, for example, patient event recorded by actuating a button or using a paper diary, and/or an auto-detected arrhythmia event), a third column 722 for date and time associated with the event type of the second column 716, a fourth column 718 for describing a symptom associated with the patient-recorded event, and a fifth column 720 for providing a type of activity (such as, walking, sitting, running, and lying down) associated with the patient-recorded event. As an exemplary illustration, the first sub-screen 710 shows the patient-recorded event 712 that was recorded on Wednesday Dec. 2, 2014 14:20:12, and was a patient button press event (that is, the event was recorded by the patient by actuating a button on an ECG recording device).

In accordance with aspects of the present specification, the ECG processing module 140 analyzes the patient-recorded events and the ECG recordings to determine if a correlation exists, in time, between the patient-recorded events and arrhythmia events detected automatically by the module 140. In some embodiments, the module 140 determines the correlation by checking if an automatically detected event exists within a predetermined time window before and after the patient-recorded event. In some embodiments, the predetermined time window ranges between 1 to 20 minutes before and between 1 to 10 minutes after a patient-recorded event. In some embodiments, the predetermined time window is 3 minutes before and 3 minutes after a patient-recorded event.

In some embodiments, if the module 140 determines a time based correlation between a patient-recorded event and an arrhythmia event automatically detected by the module 140, the module 140 associates the auto-detected arrhythmia event with the patient-recorded event and displays the auto-detected arrhythmia event bundled along with the patient-recorded event in a chronological order. As an exemplary illustration, the patient-recorded event 712 is associated and displayed together and in a chronological order with first and second auto-detected arrhythmia events 728, 730 occurring before the patient-recorded event 712. Also, third, fourth, fifth, sixth, seventh and eighth auto-detected arrhythmia events 753, 754, 755, 756, 757, 758 occurring after the patient-recorded event 712 are associated and displayed together and in a chronological order with the patient-recorded event 712. Thus, the module 140 populates the rows of the table 745 with events automatically detected (within the predetermined time window) prior to and after a patient-recorded event.

In accordance with an aspect of the present specification, the user can choose to correlate none, one, or more than one auto-detected arrhythmia events, with a patient-recorded event, occurring prior to and/or after the patient-recorded event. The user is enabled to provide his choice of correlation by selecting none, one or more than one checkboxes displayed in the first column 714. In embodiments, if the user clicks on or selects any checkbox corresponding to an auto-detected arrhythmia event, the module 140 prints (or includes) an ECG associated with the selected auto-detected arrhythmia event along with an ECG associated with the patient-recorded event in a specific section (referred to, for example, as a Patient Event—Arrhythmia Event Correlation section) of an ECG analysis report. If the user correlates an auto-detected arrhythmia event occurring before the patient-recorded event, then the ECG for that auto-detected arrhythmia event is printed (or included in the ECG analysis report) before the ECG for the patient-recorded event, and if the user correlates an auto-detected arrhythmia event occurring after the patient-recorded event, then the ECG for that auto-detected arrhythmia event is printed (or included in the ECG analysis report) after the ECG for the patient-recorded event. For example, in the table 745 the user chooses to correlate the first auto-detected arrhythmia event 728 and the sixth auto-detected arrhythmia event 756 with the patient-recorded event 712 (by selecting the checkboxes corresponding to the first and sixth auto-detected arrhythmia events 728, 756), where the first auto-detected arrhythmia event 728 occurs prior to and the sixth auto-detected arrhythmia event 756 occurs after the auto-detected arrhythmia event 712. Consequently, the ECG analysis report will have a first ECG associated with the event 728 followed by a second ECG associated with the patient-recorded event 712 which will be followed by a third ECG associated with the event 756. The GUI screen 700 also displays a second sub-screen 735 that presents an ECG waveform segment 735' corresponding to the correlated auto-detected arrhythmia event 728, followed by a third sub-screen 736 that presents an ECG waveform segment 736' corresponding to the patient-recorded event 712 and followed by a fourth sub-screen 737 that present an ECG waveform segment 737' corresponding to the correlated auto-detected arrhythmia event 756. In other words, the central third sub-screen 736 displays the ECG waveform segment corresponding to a patient-recorded event, the preceding second sub-screen 735 displays the ECG waveform segment corresponding to an auto-detected arrhythmia event correlated with and occurring before the patient-recorded event while the subsequent fourth sub-screen 737 displays the ECG waveform segment corresponding to an auto-detected arrhythmia event correlated with and occurring after the patient-recorded event.

In embodiments, the patient-recorded event is marked or highlighted in the corresponding ECG waveform segment. For example, the patient-recorded event 712 is shown marked with an indicator such as, for example, a (green) colored marker 738 in the ECG waveform segment 736'. Also, events in the prior and subsequent ECG waveform segments 735', 737' are marked with indicators such as, for example, colored markers 739, 741.

The GUI screen 700 further displays a fifth sub-screen 740 that presents a composite ECG waveform 742 comprising of the ECG waveform segment 736', corresponding to the date and time of the selected or clicked patient-recorded event 712, along with a predetermined time duration of ECG waveforms 735' and 737' before and after the ECG waveform segment 736'. This provides the user with more context of what happened in the ECG recording both before and after a selected or clicked patient-recorded event. In some embodiments, time duration of the ECG waveform segments 735', 736', 737' being displayed depends at least upon a zoom level chosen by the user and/or a size of the user's display monitor. In some embodiments, the time duration of the ECG waveform segments 735', 736', and 737' being displayed is predefined and fixed while in some embodiments the time duration may be customized by the user.

Figure 8:
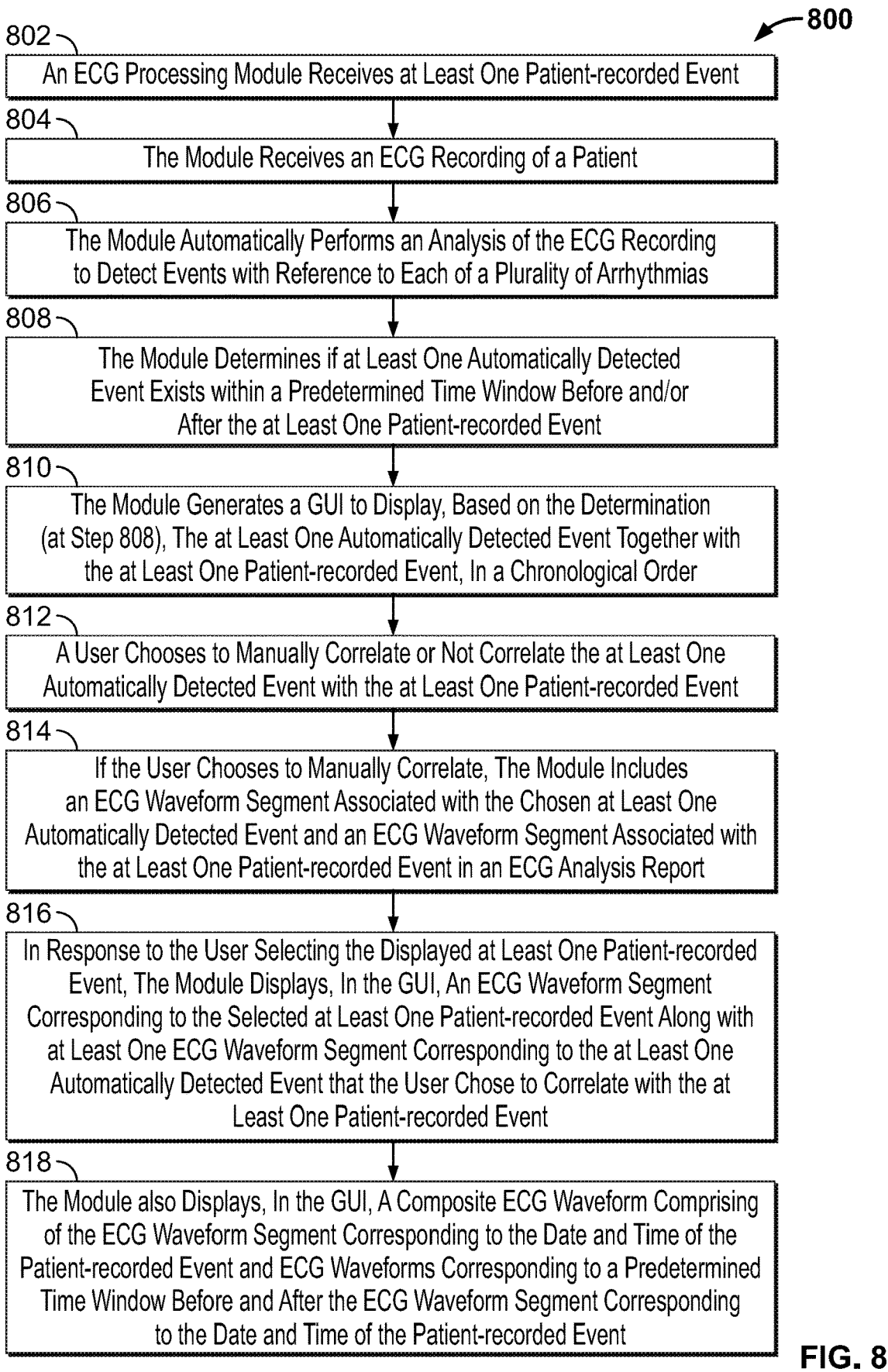
FIG. 8 is a flowchart of a method of correlating patient-recorded events with automatically detected arrhythmia events, in accordance with some embodiments of the present specification.

FIG. 8 is a flowchart of a method 800 of correlating patient-recorded events with automatically detected arrhythmia events, in accordance with some embodiments of the present specification. In embodiments, the method 800 is implemented by the ECG processing module 140 (FIG. 1). At step 802, the module 140 receives at least one patient-recorded event. At step 804, the module 140 receives an ECG recording of a patient. At step 806, the module 140 automatically performs an analysis of the ECG recording to detect events with reference to each of a plurality of arrhythmias such as, but not limited to, atrial fibrillation (AF), sinus pause or arrest, long R-R intervals, ventricular tachycardia (VT), ventricular run (V-Run), supraventricular tachycardia (SVT), supraventricular run (SV-Run), bradycardia and V-pattern including bigeminies and trigeminies.

At step 808, the module 140 determines if at least one automatically detected event exists within a predetermined time window before and/or after the at least one patient-recorded event. In some embodiments, the predetermined time window ranges between 1 to 20 minutes before and between 1 to 10 minutes after a patient-recorded event. In some embodiments, the predetermined time window is 3 minutes before and 3 minutes after a patient-recorded event.

At step 810, the module 140 generates a GUI to display, based on the determination (at step 808), the at least one automatically detected event together with the at least one patient-recorded event. In embodiments, the at least one automatically detected event and the at least one patient-recorded event are displayed together in a chronological order.

At step 812, a user chooses to manually correlate or not correlate the at least one automatically detected event with the at least one patient-recorded event. In some embodiments, the user indicates his choice of correlation (the at least one automatically detected event with the at least one patient-recorded event) by selecting or not selecting a checkbox displayed in association with the at least one automatically detected event. If the user chooses to manually correlate the at least one automatically detected event with the at least one patient-recorded event then, at step 814, an ECG waveform segment associated with the chosen at least one automatically detected event and an ECG waveform segment associated with the at least one patient-recorded event are included (in a chronological sequence relative to one another) in an ECG analysis report, by the module 140.

At step 816, in response to the user selecting the displayed at least one patient-recorded event, the module 140 displays, in the GUI, an ECG waveform segment corresponding to the selected at least one patient-recorded event along with at least one ECG waveform segment corresponding to the at least one automatically detected event that the user chose to correlate with the at least one patient-recorded event at step 812.

At step 818, the module 140 also displays, in the GUI, a composite ECG waveform comprising of the ECG waveform segment corresponding to the date and time duration of the patient-recorded event and ECG waveforms corresponding to a time duration before and after the ECG waveform segment corresponding to the date and time duration of the patient-recorded event. In various embodiments, the time duration of the ECG waveform segments being displayed depends at least upon a zoom level chosen by the chosen and a size of the user's display monitor.

In accordance with some aspects of the present specification, the ECG processing module 140 (FIG. 1) executes a plurality of sequences of programmatic instructions or code to enable or cause at least one CPU of the computing device 120 to automatically determine and set a point signifying an end of analysis (EOA) of an ECG recording.

A problem that users have with conventional ECG recording devices is that patients often do not use them correctly, resulting in long periods of unusable data. For example, a patient may remove or disconnect his ECG recording device after the device has been worn for a period of time, but the ECG recording device may continue to record signals that manifest as a stable flat line after some noise recorded as a result of disconnection of recording electrodes. Unfortunately, this is often not discovered until a user goes through all of the recorded data and determines how much is actually usable.

Accordingly, the module 140 implements an end point analysis process that identifies periods of usable data and periods of non-usable data and then, when an ECG recording device is returned by a patient, the module 140 can quickly present feedback regarding how much of the ECG monitoring period was actually useful. With that information, the patient may immediately get prescribed a new test or a new ECG recording device (rather than having the patient to go home and then return when problems are discovered with his ECG recordings).

In some embodiments, the module 140 works back from an end of the ECG recording by checking for a predetermined duration of ECG inactivity. If no ECG activity is found, the module 140 checks a preceding duration in the same way. Once the module 140 detects ECG activity (rather than background noise) an end of analysis point is set. FIG. 9A shows a GUI 900 illustrating an ECG waveform 905 having a first portion 910 of flat line (corresponding to an end of ECG recording or signal) preceded by a second portion 915 of noise data recorded during, for example, disconnection of recording electrodes. Also shown, is an end of analysis (EOA) point 920 that is automatically set and highlighted (such as, for example, by a colored dot) on the ECG waveform 905.

In some embodiments, the module 140 further enables the user to manually revise/reposition where he wants the end of analysis point 920 to be, should he not agree with the automatically determined EOA point. In some embodiments, the user can select the end of analysis point 920 to any other position on the ECG waveform 905.

Figure 10:
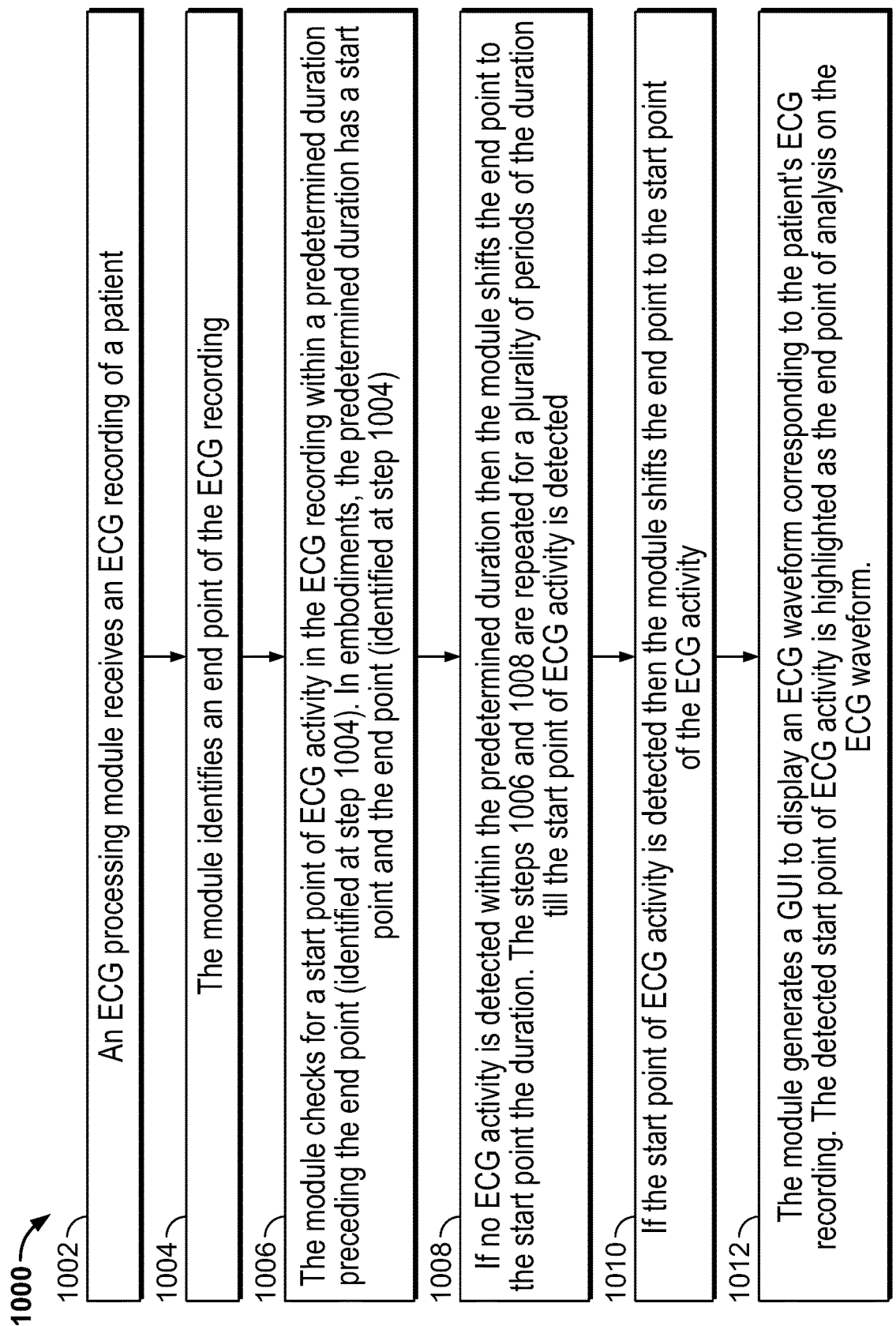
FIG. 10 is a flowchart of a method of automatically determining an end point of analysis of an ECG recording of a patient, in accordance with some embodiments of the present specification.

FIG. 10 is a flowchart of a method 1000 of automatically determining an end point of analysis of an ECG recording of a patient, in accordance with some embodiments of the present specification. In embodiments, the method 1000 is implemented by the ECG processing module 140 (FIG. 1). At step 1002, the module 140 receives the ECG recording of the patient. At step 1004, the module identifies an end point of the ECG recording. In some embodiments, the end point is based on a total duration for which the patient is required to record his ECG signals using an ECG recording device. For example, if the patient is required to record his ECG signals for a total duration of 48 hours then the end point of the ECG recording is identified as the end of the 48 hours of recording. In some embodiments, the end point is based on when the ECG recording device (device 115 of FIG. 1) stopped recording (such as, for example, due to battery exhaustion or due to its memory being full).

At step 1006, the module 140 checks for a start point of ECG activity in the ECG recording within a predetermined duration preceding the end point (identified at step 1004). In embodiments, the predetermined duration has a start point and the end point (identified at step 1004). If no ECG activity is detected within the predetermined duration then, at step 1008, the module 140 shifts the end point to the start point of the duration. In various embodiments, a flat line as well as a noise signal is considered as ECG inactivity. In embodiments, the steps 1006 and 1008 of checking for the start point of ECG activity and shifting of the end point to the start point of the duration, respectively, are repeated for a plurality of periods of the duration till the start point of ECG activity is detected.

If the start point of ECG activity is detected then, at step 1010, the module 140 shifts the end point to the start point of the ECG activity. In other words, the module 140 determines the start point of ECG activity and automatically establishes the start point of ECG activity as the end point of analysis of the ECG recording. In other words, the module 140 identifies and sets the end point of the ECG activity as the last region of detected ECG that is usable (that is, looks like ECG, is not flat line and is not just electrical noise).

At step 1012, the module 140 generates a GUI to display an ECG waveform corresponding to the patient's ECG recording. The detected start point of ECG activity is highlighted as the end point of analysis on the ECG waveform.

In some embodiments, the module 140 further enables the user to manually re-shift or reposition (on the GUI) the automatically established end point of analysis, to a different position, if the user does not agree with the automatically determined end point of analysis. To do so, in some embodiments, the user can click on and select the end point of analysis highlighted on the ECG waveform, in the GUI, and drag the selected end point of analysis to the different position/point on the ECG waveform.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A computer readable non-transitory medium comprising a plurality of executable programmatic instructions wherein, when the plurality of executable programmatic instructions are executed by a processor, a process for prioritizing electrocardiogram (ECG) analyses is performed, the plurality of executable programmatic instructions comprising:
  programmatic instructions, stored in the computer readable non-transitory medium, for receiving an ECG recording of a patient for a first duration;
  programmatic instructions, stored in the computer readable non-transitory medium, for automatically performing a first analysis of the ECG recording for the first duration to detect events indicative of at least one of a plurality of arrhythmias within the first duration;
  programmatic instructions, stored in said computer readable non-transitory medium, for generating a graphical user interface (GUI) defined by a single screen having a plurality of segmented areas, wherein—
    in a first of the plurality of segmented areas, the GUI is configured to display heart rate data corresponding to the first duration;
    in a second of the plurality of segmented areas, the GUI is configured to display the automatically detected events indicative of at least one of the plurality of arrhythmias, wherein, when displayed, each of the automatically detected events is displayed as a vertical line, a width of each of the vertical lines being indicative of a duration of the automatically detected events, and wherein each of the automatically detected events is visually aligned with a corresponding one of the heart rate data in the first of the plurality of segmented areas; and
    in at least a third of the plurality of segmented areas the GUI is further configured to display an ECG waveform segment in a response to a selection of at least one of the automatically detected events;
  programmatic instructions, stored in the computer readable non-transitory medium, for enabling a user to select at least one of the ECG waveforms of a second duration;
  programmatic instructions, stored in the computer readable non-transitory medium, for presenting the user with at least one option in response to the user's selection of the at least one of the ECG waveforms;
  programmatic instructions, stored in said computer readable non-transitory medium, for performing a second analysis of the at least one of the ECG waveforms of the second duration in response to the user's selection of the at least one option; and programmatic instructions, stored in said computer readable non-transitory medium, for displaying at least one output corresponding to the second analysis.

2. The computer readable non-transitory medium of claim 1, wherein the first duration is up to 30 days.

3. The computer readable non-transitory medium of claim 1, wherein the plurality of arrhythmias comprises at least one of atrial fibrillation (AF), sinus pause or arrest, long R-R intervals, ventricular tachycardia (VT), ventricular run (V-Run), supraventricular tachycardia (SVT), supraventricular run (SV-Run), bradycardia or V-pattern including at least one of bigeminies and trigeminies.

4. The computer readable non-transitory medium of claim 1, wherein the second duration is up to 7 days.

5. The computer readable non-transitory medium of claim 1, wherein the second analysis comprises performing at least one of a ST-analysis, a QT-analysis, a heart rate variability analysis, a screening of recordings for sleep apnea, or a superimposition of heartbeats.

6. The computer readable non-transitory medium of claim 1, wherein the GUI is configured to display the ECG waveform segments in a descending order of severity, as determined based on their corresponding automatically detected events.

7. The computer readable non-transitory medium of claim 6, wherein the GUI is adapted to display up to 10 ECG waveform segments.

8. The computer readable non-transitory medium of claim 6, wherein the GUI is adapted to be updated with an ECG waveform segment for a next most severe detected event if a displayed ECG waveform segment is deleted or if its severity is re-classified.

9. The computer readable non-transitory medium of claim 1, further comprising programmatic instructions for generating a visible area to display a composite ECG waveform comprising of a selected ECG waveform segment and ECG waveforms corresponding to a predetermined time duration before and/or after the selected ECG waveform segment.

10. The computer readable non-transitory medium of claim 1, wherein the GUI is adapted to display a count of a total number of automatically detected events.

11. The computer readable non-transitory medium of claim 1, further comprising programmatic instructions for generating a plurality of data based on the first analysis and for automatically generating textual information using the plurality of data, wherein the plurality of data includes at least one of a total time duration of an analyzed ECG recording, a percentage of the total time duration excluded due to artifacts, a ventricular beat burden, a supraventricular beat burden, a count of events detected for each of the plurality of arrhythmias, or one or more statistics related to the events detected for each of the plurality of arrhythmias.

12. The computer readable non-transitory medium of claim 11, further comprising programmatic instructions for displaying, in the GUI, the generated textual information and programmatic instructions for integrating the textual information into a report upon selection of an option within the GUI.

13. The computer readable non-transitory medium of claim 11, further comprising programmatic instructions for dynamically updating the generated textual information if one or more automatically detected events are deleted or re-classified.

14. A computer readable non-transitory medium comprising a plurality of executable programmatic instructions wherein, when the plurality of executable programmatic instructions are executed by a processor, a process for presenting electrocardiogram (ECG) analyses is performed and wherein the plurality of executable programmatic instructions comprise:

programmatic instructions adapted to receive an ECG recording of a patient, wherein the ECG recording has a first duration;

programmatic instructions adapted to perform a first analysis of the ECG recording to detect events indicative of at least one arrhythmia;

programmatic instructions adapted to generate at least one graphical user interface (GUI), wherein the at least one GUI is configured to display heart rate data in a first portion of the GUI, configured to display the detected events indicative of the at least one arrhythmia in a second portion of the GUI, wherein the detected events are visually aligned with corresponding heart rate data, wherein each of the detected events is displayed as a vertical line, and wherein a width of each of the vertical lines is indicative of a duration of the detected events, and configured to display ECG waveform segments in a third portion of the GUI in response to selecting at least one of the detected events;

programmatic instructions adapted to enable a user to select at least one of the ECG waveforms;

programmatic instructions adapted to present the user with at least one option in response to the selection of the at least one of the ECG waveforms;

programmatic instructions adapted to perform a second analysis of the at least one of the ECG waveforms in response to the selection of the at least one option; and programmatic instructions adapted to display at least one output corresponding to the second analysis.

15. The computer readable non-transitory medium of claim 14, wherein the at least one arrhythmia is at least one of an atrial fibrillation (AF), a sinus pause or arrest, a long R-R interval, a ventricular tachycardia (VT), a ventricular run (V-Run), a supraventricular tachycardia (SVT), a supraventricular run (SV-Run), a bradycardia or a V-pattern including at least one of bigeminies and trigeminies.

16. The computer readable non-transitory medium of claim 14, wherein the second analysis comprises at least one of a ST-analysis, a QT-analysis, a heart rate variability analysis, a screening of recordings for sleep apnea, or a superimposition of heartbeats.

17. The computer readable non-transitory medium of claim 14, wherein the GUI is configured to display ECG waveform segments corresponding to each of the detected events in an order of descending severity.

18. The computer readable non-transitory medium of claim 17, wherein the GUI is adapted to be updated with an ECG waveform segment for a next most severe detected event if a displayed ECG waveform segment is removed or if its severity is re-classified.

19. The computer readable non-transitory medium of claim 14, further comprising programmatic instructions adapted to generate a composite ECG waveform comprising a selected ECG waveform segment and ECG waveforms corresponding to a predetermined time duration before and/or after the selected ECG waveform segment.

20. The computer readable non-transitory medium of claim 14, wherein the GUI is adapted to display a count of a total number of automatically detected events.

21. The computer readable non-transitory medium of claim 14, further comprising programmatic instructions adapted to generate data based on the first analysis and generate textual information using the data, wherein the data comprises at least one of a total time duration of an analyzed ECG recording, a percentage of the total time duration excluded due to artifacts, a ventricular beat burden, a supraventricular beat burden, a count of events detected for each of a plurality of arrhythmias, or one or more statistics related to the events detected for each of the plurality of arrhythmias.

22. The computer readable non-transitory medium of claim 21, further comprising programmatic instructions adapted to cause the GUI to display the generated textual information and programmatic instructions adapted to integrate the textual information into a report upon selection of an option within the GUI.

23. The computer readable non-transitory medium of claim 21, further comprising programmatic instructions adapted to dynamically update the generated textual information if one or more detected events are deleted or re-classified.

* * * * *